(12) United States Patent
Shoudy et al.

(10) Patent No.: US 12,161,888 B2
(45) Date of Patent: Dec. 10, 2024

(54) ULTRASONIC BEAM PATH DETERMINATION AND TARGETING

(71) Applicant: General Electric Company, Schenectady, NY (US)

(72) Inventors: David Andrew Shoudy, Niskayuna, NY (US); Jeffrey Michael Ashe, Gloversville, NY (US); Warren Lee, Niskayuna, NY (US); Ying Fan, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 127 days.

(21) Appl. No.: 17/161,022

(22) Filed: Jan. 28, 2021

(65) Prior Publication Data

US 2022/0233886 A1    Jul. 28, 2022

(51) Int. Cl.
*A61N 7/00* (2006.01)

(52) U.S. Cl.
CPC ........ *A61N 7/00* (2013.01); *A61N 2007/0043* (2013.01); *A61N 2007/0052* (2013.01); *A61N 2007/0078* (2013.01); *A61N 2007/0082* (2013.01)

(58) Field of Classification Search
CPC .............. A61N 7/00; A61N 2007/0043; A61N 2007/0052; A61N 2007/0078; A61N 2007/0082
See application file for complete search history.

(56) References Cited

U.S. PATENT DOCUMENTS

| | | | |
|---|---|---|---|
| 6,623,432 B2 | 9/2003 | Powers et al. | |
| 7,063,666 B2 | 6/2006 | Weng et al. | |
| 7,662,114 B2 | 2/2010 | Seip et al. | |
| 8,622,937 B2 | 1/2014 | Weng et al. | |
| 9,433,396 B2 | 9/2016 | Ridley et al. | |
| 10,231,712 B2 | 3/2019 | Ebbini et al. | |
| 2003/0028111 A1 | 2/2003 | Vaezy et al. | |
| 2004/0068186 A1 | 4/2004 | Ishida et al. | |

(Continued)

FOREIGN PATENT DOCUMENTS

| | | |
|---|---|---|
| JP | H0816435 B2 | 2/1996 |
| JP | H0966057 A | 3/1997 |

(Continued)

OTHER PUBLICATIONS

International Search Report and Written Opinion for PCT Application No. PCT/US2022/013066 mailed May 11, 2022, 10 pgs.

(Continued)

*Primary Examiner* — Patricia J Park
(74) *Attorney, Agent, or Firm* — Fletcher Yoder, P.C.

(57) ABSTRACT

The present discussion relates to the delivery of ultrasonic therapy energy to a target region in conjunction with a clear path determination that may assess one or more of: (1) presence of non-soft tissue regions within the therapy beam path (e.g., bone or bone-like structures, gas-filled cavities, and so forth), (2) partial "lift-off" of the probe head; or (3) sufficiency of acoustic coupling. Upon determination or confirmation of at least a partial clear path with respect to some or all of these factors, the therapy beam may be delivered to the target region.

25 Claims, 17 Drawing Sheets

(56) References Cited

U.S. PATENT DOCUMENTS

| | | | |
|---|---|---|---|
| 2008/0183077 A1* | 7/2008 | Moreau-Gobard | A61B 8/4209 600/439 |
| 2010/0069753 A1 | 3/2010 | Fedewa | |
| 2010/0228126 A1* | 9/2010 | Emery | A61B 8/08 600/439 |
| 2012/0157842 A1* | 6/2012 | Davis | A61B 8/08 600/439 |
| 2012/0172708 A1* | 7/2012 | Anand | A61B 8/5223 600/411 |
| 2012/0209118 A1 | 8/2012 | Warnking | |
| 2013/0184728 A1* | 7/2013 | Mishelevich | A61B 8/0808 606/169 |
| 2014/0081142 A1 | 3/2014 | Toma et al. | |
| 2014/0213903 A1* | 7/2014 | Seo | A61B 8/5207 601/3 |
| 2015/0032128 A1* | 1/2015 | Tavlin | A61N 7/02 606/131 |
| 2015/0359603 A1* | 12/2015 | Levy | A61N 7/02 703/2 |
| 2017/0027645 A1* | 2/2017 | Ben Oren | A61B 18/22 |
| 2018/0028841 A1* | 2/2018 | Konofagou | A61N 7/02 |
| 2019/0060675 A1* | 2/2019 | Krone | A61N 7/00 |
| 2019/0160309 A1* | 5/2019 | Ebbini | A61N 7/00 |
| 2019/0269367 A1* | 9/2019 | Reinders | A61B 18/24 |
| 2019/0380679 A1 | 12/2019 | Bharat et al. | |
| 2021/0000541 A1* | 1/2021 | Levy | A61B 34/10 |
| 2021/0282748 A1* | 9/2021 | Stehle | G01S 15/8915 |

FOREIGN PATENT DOCUMENTS

| | | |
|---|---|---|
| JP | 2006204929 A | 8/2006 |
| JP | 2011206451 A | 10/2011 |

OTHER PUBLICATIONS

"HIFUPlex™ Portfolio", Sonic concepts retrieved from https://sonicconcepts.com/hifuplex/ on Aug. 20, 2020.

JP application 2023-545224 filed Jul. 26, 2023—Office Action issued May 8, 2024; Machine Translation; 8 pages.

JP2006204929 English Abstract; Espacenet Aug. 2, 2024; 1 page.

JPH08164135 English Abstract; Espacenet Aug. 2, 2024; 1 page.

JPH0966057 English Abstract; Espacenet Aug. 2, 2024; 1 page.

* cited by examiner

ULTRASONIC BEAM PATH DETERMINATION AND TARGETING

BACKGROUND

The subject matter disclosed herein relates to identifying, targeting and/or dosing regions of interest in a subject via application of energy (e.g., neuromodulating energy) to cause targeted physiological outcomes. In particular, the disclosed techniques may be useful in accurately delivering a known dose to a targeted region.

Neuromodulation has been used to treat a variety of clinical conditions. However, specific tissue targeting via neuromodulation may be challenging. For example, accurate focusing of neuromodulating energy may vary based on individual patient anatomy. Certain patients may have variations in organ size or location relative to other patients based on their height, weight, age, gender, clinical condition, and so forth, which may impact targeting and dose delivery when using various neuromodulation techniques.

In the context of neuromodulation using ultrasonic devices, other common challenges with delivering accurate ultrasonic therapy at a prescribed dose include poor acoustic coupling between the therapy probe and the patient, "lift off" of a portion of the probe from the patient, or presence of an acoustic reflector or absorber (e.g., bone structures, such as ribs, bowel gas, and so forth) in the therapy beam path. Such factors can result in delivery of an inaccurate dose amount and/or lead to patient discomfort.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, an ultrasonic therapy delivery system is provided. In accordance with this embodiment, the ultrasonic therapy delivery system comprises an energy application device configured to deliver ultrasonic energy to a target region in a subject, the energy application device comprising one or more transducers configured to emit an imaging beam and a therapy beam and a controller. The controller is configured to perform actions comprising: activating some or all of the one or more transducers to emit the imaging beam; receiving image data generated in response to the imaging beam; determining whether all or part of the target region is present in the image data scanned by the imaging beam; in response to determining that at least a portion of the target region is present in the image data, determining whether the therapy beam can be applied to the target region to administer all or part of a therapy dose of ultrasonic energy to the target region; and in response to determining that the therapy beam can be applied to the target region to administer the therapy dose, activating some or all of the one or more transducers to emit the therapy beam to administer all or part of the therapy dose to the target region.

In another embodiment, a method of delivery of ultrasonic therapy energy is provided. In accordance with this method, image data of a subject is acquired using an ultrasonic imaging beam. A determination is made whether all or part of a target region for therapy is present in the image data. In response to determining that at least a portion of the target region is present in the image data, a determination is made whether an ultrasonic therapy beam can be applied to the target region to administer all or part of a therapy dose of ultrasonic energy to the target region. A path of the ultrasonic therapy beam at least partially overlaps a path of the ultrasonic imaging beam within the subject. In response to determining that the ultrasonic therapy beam can be applied to the target region to administer the therapy dose, one or more transducers are activated to emit the ultrasonic therapy beam to administer all or part of the therapy dose to the target region of the subject.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
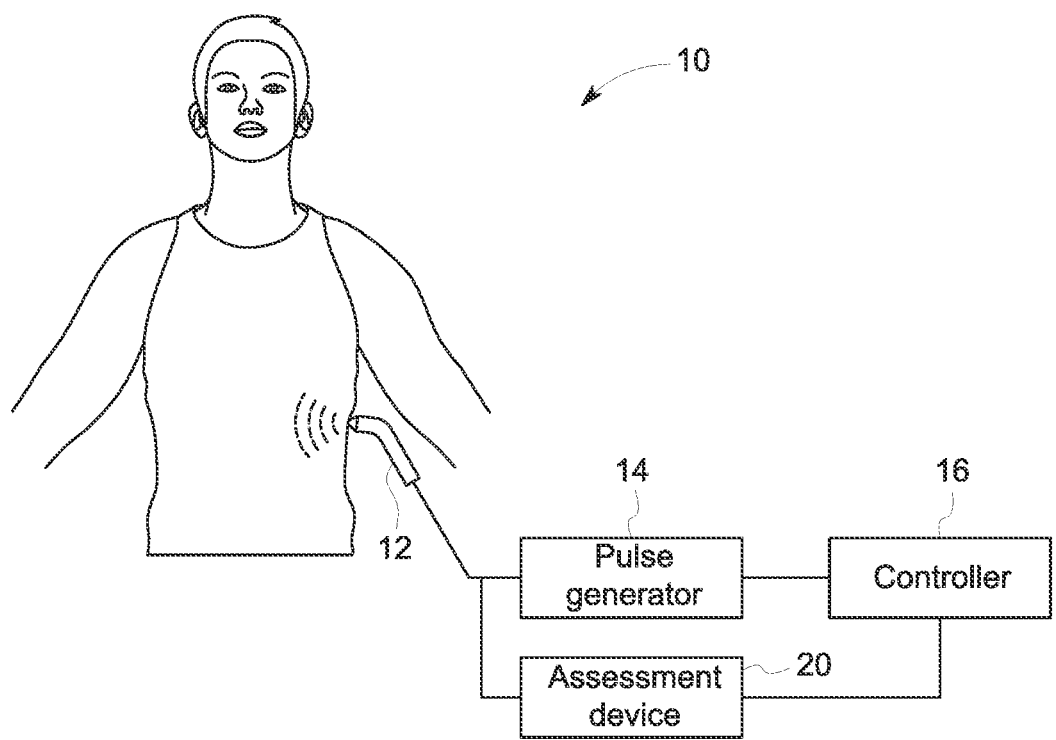
FIG. 1 is a schematic representation of a clear path determination and therapy delivery system according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

As discussed herein, one issue that can arise in using image-based techniques to evaluate or guide the application of ultrasonic therapy energy to a target region within a patient (such as for the purpose of neuromodulation) is "blind spots" that may be correspond to regions of the patient that are traversed by the therapy beam but not seen by the imaging technique. As used herein, the path of the therapy beam (i.e., the therapy beam path) encompasses areas "from-to-beyond" the target region (i.e., from the transducer to the target region and beyond the target region) in addition to objects or structures near the target region. For practical purposes, the therapy beam may be envisioned as a cone that converges from the transducer to the target region and another cone that diverges from the target region to beyond. With respect to blind spots traversed by the therapy beam along this path but not imaged by the imaging beam, these blind spots may lead to the therapy modulating "off target" (i.e., affecting or applying energy to patient regions that are not part of the target region) and/or failing to deliver the prescribed dose to the patient. By way of example, for a centered imaging array and outlying therapy array(s) that are applied close to or adjacent the patient skin, patient areas near the skin line may be unobserved by the imaging array but traversed by the therapy beam. Such blind spots may therefore be problematic in an image-guided therapy context.

Further, other challenges with delivering accurate and safe ultrasonic therapy using image-guided techniques may include poor acoustic coupling between the treatment device and patient, "lift off" of a portion of the treatment device relative to the patient, and the presence of an acoustic reflector or absorber (e.g., bone structures such as ribs, gas-filled pockets or regions, such as bowel gas) in the therapy beam path. With respect to these factors, poor acoustic coupling may manifest as an overly blurry or dim image, though not necessarily at an edge of the image, which may be more indicative of a "lift off" event. Partial "lift off" may be indicated by no image or a dim image along an edge of the image and may result in therapy transducer heating and reduced dose delivery. Acoustic reflection or absorption (e.g., "shadowing") may occur when the transducer(s) are over the shadow-causing structure (e.g., ribs). Such factors can result in delivery of an inaccurate dosing and/or may lead to patient discomfort.

Further, the ultrasound pressure wave creates a mechanical force that is applied to the internal tissues. If this mechanical force becomes too great, there is the potential to create undesired mechanical bioeffects. The ultrasound beam can also cause internal tissues to heat up as the tissue absorbs the ultrasound energy. Factors such as increased power or effective duty cycle cause greater internal heating. If the internal heating is too large, a number of undesired thermal bioeffects may result. In addition, tissue attenuation and acoustic impedance vary across different tissue types. For example, bone attenuation and impedance are ~15× and ~5× greater, respectively, than the next highest internal soft tissue. Much of the focus around ultrasound safety with bones results from this extreme difference, where the high attenuation can result in heating of the bone, and the high difference in acoustic impedance creates strong reflections at tissue/bone interfaces that can result in defocusing or redirecting the acoustic energy. Additionally, internal gas structures, when excited with a high mechanical force, may cavitate, which may affect surrounding tissues.

Due to the issues noted above, as well as to ensure accurate dose delivery (and thus effective therapy), it is desirable to know if there is a "clear" path with respect to the therapy beam path up to and beyond the target region. Such a path determination or analysis may encompass a multitude of factors (e.g., an absence of bone or otherwise dense, acoustically reflective structures, an absence of gas filled cavities, an absence of other anatomies that are undesirable for receiving a portion of the ultrasonic energy, good acoustic coupling, no "lift off" of the probe interface, and so forth) that may or may not all be considered in a given path determination. Which factor(s) are considered may depend on considerations such as the therapy protocol, the patient anatomy, the system geometry, the prescribed frequencies and/or dose, and so forth. Further, in some implementations a path determination or analysis may span a range of acceptability for some or all of the various factors considered, either in isolation or in combination, such that the determination may not be a simplistic binary "clear/not clear" determination but a graduated or quantified clearance metric. In such contexts the extent of the determined "clear" path may in turn be leveraged to determine a suitable next step, such as notification to a user to reposition and/or reorient the energy application device or electronic manipulation of the application device elements to leverage the information in the path determination, such as by adjusting a power level at which the device is operated, sweeping one or more transducers within the device to adjust the path, selectively activating a subset of the available transducers, and so forth. In practice, evaluation and use of the path determination, either in a binary or graded form, may utilize various criteria or comparisons, such as safety criteria, a therapy dose criteria (e.g., based on the degree and characteristics of the therapy dose that can be applied in view of the observed clear path measure, corresponding to, based on predictive analytics, how much dose energy or power will be delivered to the target region and what the ultrasound beam profile will look like (i.e., spatially where will the energy be delivered, will the beam look like a regular focused beam, does an obstruction defocus the energy into a larger area, or does the beam shift to an unintended location)), and/or an effectiveness threshold (e.g., that the dose that can be applied to the target region along the evaluated path can provide sufficient dose or energy to exceed a specified threshold effectiveness based on what is determined can be delivered taking into account any obstruction(s) and the beam characteristics being evaluated as well as clinical factors such as the particular target anatomy, patient, and prescription).

While various factors may be considered as part of a path determination or analysis as discussed herein, in certain embodiments such a determination may include (primarily or as one component) a determination that the target region for therapy is "visible" (i.e., lies within the imaging beam), and thus is accessible to the therapy beam. By way of example, an initial aspect of a path determination or analysis may be whether or not the target region (either partially or completely) is present within the path imaged by the imaging beam. In such a context the absence of any portion of the target region within the imaged region seen by the imaging beam may preclude evaluation of further factors. That is, if the target region is not visible to the imaging beam, there is presumed to be no path for the therapy beam to the target region, and further path considerations may be ignored. In some contexts, evaluation of whether the target region is visible to the imaging beam may be the only consideration. In other embodiments, additional factors (e.g., "lift off" events, acoustic coupling) may be evaluated as long as some or all of the target region is visible in the imaging beam. Further, the extent of the target region visible to the imaging beam (if less than total) may be compared to a threshold for effectiveness or a therapy dose criterion to determine if the available path is sufficient for application of the therapy beam along the path.

With this in mind, the techniques and approaches discussed herein comprise combinations of physical embodiments and control/analysis schemes that may be employed to provide for the safe and accurate delivery of the ultrasound therapy to the target. Indeed, while the presently described techniques and approaches may be useful to a trained technologist administering a ultrasonic therapy treatment to a target region of a patient, these techniques and approaches may also be employed to allow a medically untrained individual, including the patient themselves, to safely administer an ultrasonic therapy treatment without risk of injury and while achieving the desired medical effect.

To that end, the disclosed beam path analysis and determination techniques may be used in conjunction with an ultrasonic therapy system (e.g., a neuromodulation system) configured to be used to deliver ultrasonic energy as part of a treatment protocol. By way of example, FIG. 1 is a schematic representation of a system 10 for neuromodulation to achieve neuromodulating effects such as neurotransmitter release and/or activation of components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive, e.g., via leads or wireless connection, or otherwise generate energy pulses that in use are directed to a target region in an internal tissue or an organ of a subject, which in turn results in a targeted physiological outcome (e.g., release of a neurotransmitter, protein, and so forth).

In certain embodiments, the energy application device 12 and/or the pulse generator 14 may communicate wirelessly, for example with a controller 16 that may in turn provide instructions to the pulse generator 14. In other embodiments, the energy application device 12 may be an extracorporeal device, e.g., may operate to apply energy transdermally or in a noninvasive manner from a position outside of a subject's body, and may, in certain embodiments, be integrated with the pulse generator 14 and/or the controller 16. In embodiments in which the energy application device 12 is extracorporeal, the energy application device 12 may be operated by a caregiver, or the patient, and positioned at a spot on or above a subject's skin such that the energy pulses are delivered transdermally to a desired internal tissue. Once positioned to apply energy pulses to the desired site, the system 10 may initiate neuromodulation of one or more nerve pathways to achieve targeted physiological outcome or clinical effects. In some embodiments, the system 10 may be implemented such that some or all of the elements may communicate in a wired or wireless manner with one another.

In certain embodiments, the system 10 may include an assessment device or logic 20 that is coupled to the controller 16 and that assesses characteristics that are indicative of whether a clear or sufficient path exists to the target region with respect to the placement and orientation of the energy application device 12. As used herein, such path analysis may include some or all of: a determination of sufficient acoustic coupling, a determination that there is no "lift off" in which a portion of the probe is not in contact with the patient, and a determination that there are no or limited blocking anatomies or structures between the probe and target region (e.g., bone or bone-like structures, gas-filled cavities, and so forth). In one embodiment, the assessment device or logic 20 may utilize different frequencies of ultrasonic energy emitted by the same transducer or transducers of the energy application device 12 to perform therapy and imaging. In other embodiments, the therapeutic and assessment frequencies of ultrasonic energy may be emitted by different transducers (e.g., image transducers and therapy transducers) or structures on the energy application device 12. In addition, non-image sensing modalities (e.g., electrodes, pressure sensors, cavitation sensors and so forth) may also generate data or measurements used to help determine one or more of the path factors that are evaluated.

Based on the path assessment, delivery of therapeutic ultrasonic energy may be altered, modulated, or steered automatically to achieve the prescribed therapeutic result. In addition or in the alternative, an indication or guidance may be provided to the users, such as via audible or visible indicators, to indicate the presence or absence of a sufficiently clear or suitable path for the therapeutic ultrasonic energy or to provide guidance regarding placement and/or orientation of the energy application device 12 so as to achieve such a path.

The system 10 as provided herein may provide energy pulses according to various modulation parameters as part of a treatment protocol to apply the effective amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for 1 minutes to 1 hour, and may be repeated at regular intervals (e.g., 72 hour intervals). In certain embodiments, energy may be delivered at a higher frequency (e.g., at 2 or 3 hour intervals) for shorter durations (e.g., 1 minutes). The application of energy, in accordance with modulation parameters, such as the treatment duration, frequency, and amplitude, may be adjustably controlled to achieve a desired result.

Figure 2:
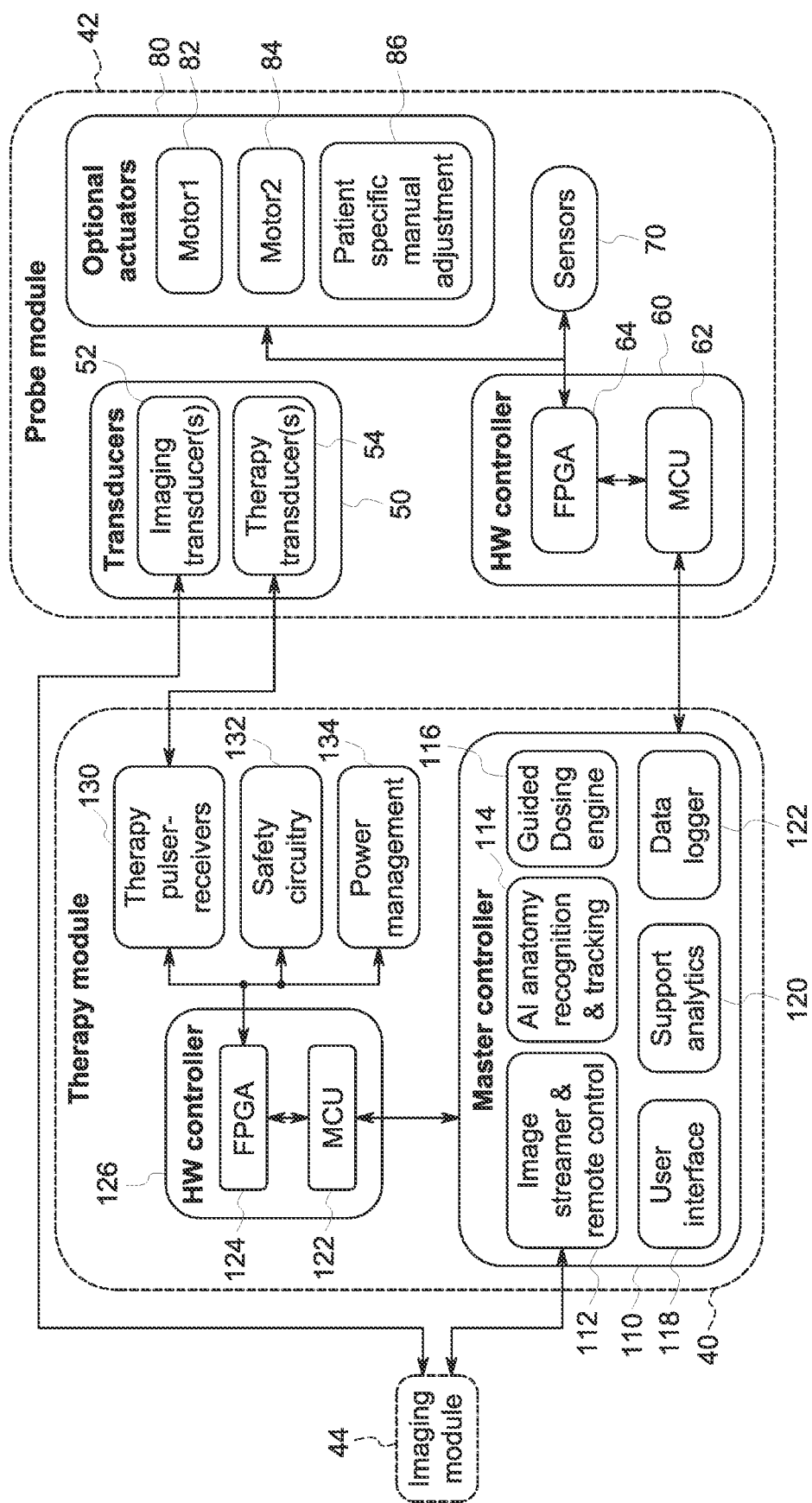
FIG. 2 is a block diagram of a clear path determination and therapy delivery system according to embodiments of the disclosure.

FIG. 2 is a block diagram of certain components of one implementation of the system 10. In particular, aspects and components of an implementation of the system 10 are shown as modules corresponding to certain functionalities described above with respect to the energy application device 12, the pulse generator 14, the assessment component 20, and/or the controller 16. For example, the block diagram of FIG. 2 illustrates a therapy module 40 and a probe module 42 which may be used to perform functions described herein with respect to FIG. 1. An imaging module 44 is also illustrated, though it may be appreciated that in certain embodiments such an imaging module 44 may be absent. In such alternative embodiments analytics performed on data acquired at what may be understood to be imaging frequencies of ultrasonic energy may be performed on unreconstructed (i.e., raw) imaging data, without reconstruction into images or analysis performed on images. By way of example, path determination or analysis as discussed herein based on data acquired using the imaging transducers 52 or at the imaging module 44 may be based on reconstructed images (e.g., signatures within the reconstructed data) or based on ultrasound signatures present in the unreconstructed image data.

Beginning with the probe module 42, in the depicted example the probe module 42 includes transducers 50. In the depicted example, the transducers 50 include both imaging transducers 52 (operating at one frequency or range of frequencies) and therapy transducers 54 (which may operate at the same or a different frequency or range of frequencies than the imaging transducers 52). In one embodiment the transducers 52 may include 128 imaging transducers and 4 therapy transducers, though other quantities or either type of transducer may instead be employed. In a simplified ultrasound signaling context, ultrasound may be serially transmitted and received via regional or defined portions of the imaging transducer array and/or therapy transducer array.

In alternative embodiments, transducers 50 may instead comprise one or more type of transducer 52 capable of operating at both the respective imaging and therapy frequencies such that separate transducers are not provided for each type of respective operation. By way of example, the transducer 52 in this context may be configured to operate at the same frequency or frequency range for both imaging and therapy operations or may be configured to operate at a first frequency range for imaging and a second frequency range for therapy. In such embodiments the single transducer or type of transducer may be operated to both provide therapy and acquire imaging-type data used in the clear path determination discussed herein. Such single transducer type approaches may be suitable in contexts where the target region is shallow and/or high power is not necessitated.

With respect to the imaging transducers 52 and therapy transducers 54, in practice the imaging transducers 52 may operate at higher frequency and/or have smaller apertures sizes relative to the therapy transducers 54. In contrast, the therapy transducers 54 will typically operate at lower frequency (for less attenuation) and/or over a larger area (for greater focusing gain) to deliver more power to deeper targets. In one implementation, the therapy transducer(s) 54 may operate at a frequency within 0.2 MHz to 2 MHz (such as 0.5 MHz or 2 MHz). In such an embodiment, the therapy transducer(s) 54 may be constructed from a suitable material, such as a piezoelectric material such as (but not limited to) PZT-4. In one implementation, the imaging transducer(s) 52 may operate in a frequency range from 2 MHz to 12 MHz (such as from 3 to 10 MHz or 5 to 12 MHz). In such an embodiment, the imaging transducer(s) 52 may be constructed from a suitable material, such as a piezoelectric material such as (but not limited to) PZT-5.

In the depicted example the probe module 42 also includes a hardware controller 60, which in the depicted example includes a microcontroller(s) (MCU) 62 in communication with a master controller (e.g., processor) 110 of the therapy module 40 and a field-programmable gate array (FPGA) 64 in communication with the MCU 62 and sensors 70 and/or actuators 80 associated with the probe module 42. In this configuration the MCU 62 and FPGA 64 may bi-directionally communicate with components of the master controller 110 (e.g., data logger 122) to coordinate and/or record operation of aspects of the probe module 42 or components associated directly or indirectly with the probe module 42, such as actuators 80 and/or sensors 70. Though shown as part of the probe module 42 in FIG. 2, it should be appreciated that some or all of the actuators 80 and/or sensors 70, if present, may be provided separate from or external to the probe module 42, e.g., as separate pieces or components. Alternatively, some or all of the actuators 80 and/or sensors 70, if present, may be provided internal to or integral with the probe module 42.

With respect to the actuators 80, in the depicted example, the actuators may include one or both of a first motor 82 and a second motor 84. One or both of the motors may be configured to move the probe module 42 itself and/or separate aspects of the probe module 42, such as the imaging transducers 52 and/or therapy transducers 54. The motors 82, 84 may, in particular, be configured to effectuate movement of the probe module 42, imaging transducers 52, and/or therapy transducers 54 in an automated manner in response to signals from the FPGA 64 provided as part of the hardware controller 60, thereby allowing communications received from the therapy module 40 to control motion of the respective components. In addition, as shown in FIG. 2, in certain embodiments a manual adjustment mechanism 86 (e.g., a patient-specific manual adjustment) such as a belt, cinch, manual placement interface, and so forth, may be provided to allow manual adjustment or movement of the probe module 42 with respect to an interface region on the patient.

With respect to the sensors 70, various types of sensors may be integrated with or, if separate, in communication with the probe module 42. By way of example the sensors 70 may include one or more of a respiration sensor, a posture and motion sensor, electrodes, pressure sensors, accelerometers, and/or a safety sensor. For example, a respiration sensor may be used to acquire quantitative or qualitative data related to patient respiration, and thereby identify periods of respiratory motion, which may be useful in identifying times when a path determination or analysis can or should be performed or when therapy may be applied. Similarly, a posture and motion sensor may be used to identify patient voluntary or involuntary motion, patient position, and patient posture or orientation. Such information may also be used to identify times when a path determination or analysis can or should be performed or when therapy may be applied. A safety sensor may be calibrated to send a signal when a safety condition or threshold is breached. Signals from this sensor may therefore be used to control (e.g., cease) operation of the probe module 42 until the safety condition is once again met. Further, and as discussed herein, electrodes, pressure sensors, and other such sensors may be employed to determine or analyze certain factors that may contribute to a path analysis or determination routine (such as determining the sufficiency of acoustic coupling, determining if a "lift off" event has occurred, and so forth). Such sensor data may be employed in addition to or instead of analysis of the image data to determine if these conditions exist or their extent if present. As shown in FIG. 2, the one or more sensors 70, if present, may be communicatively coupled to the FPGA 64 or otherwise to the hardware controller 60.

Regarding the therapy module 40, as previously noted implementations of the therapy module 40 may include a master controller (e.g., processor) 110 which may itself include or execute various sub-modules or routines. In this example the master processor includes or executes modules or routines providing functionality for an image streamer and remote control 112, artificial intelligence (AI) anatomy recognition and tracking 114, a guided dosing engine 116, a user interface 118, support analytics 120, and a data logger 122, which in this example is shown as being in communication with the MCU 62 or the probe module 42.

As with the probe module, in certain embodiments the therapy module 40 may include a hardware controller 126 which may include its own MCU 122 and FPGA 124. While depicted as separate modules for the purpose of illustration and explanation, in practice the probe module 42 and therapy module 40 may actually be one and the same (i.e., an integral structure or device configured to perform the functions of both the therapy module and probe module as discussed herein). With this in mind, though discussed separately herein, in practice the hardware controllers 60 and 126 may be implemented as a single hardware controller. In the depicted example the MCU 122 is depicted as being in communication with the master controller 110 and its components and modules. The FPGA 124 communicates with and/or controls other components of the therapy module, such as therapy pulser-receivers 130 (depicted as being in communication with the therapy transducers 54 of the probe module 42), safety circuitry 132, and/or power management circuitry 134.

In practice, the master controller 110 in conjunction with the hardware controllers 60, 126 may control operation of the therapy module 40 and probe module 42, such as to perform path determination and analysis, in addition to application of therapy, in accordance with processes and structures described herein. By way of example, the master controller 110 may in some embodiments be used to perform a path determination or analysis as discussed herein and may work with hardware controllers 126, 60 to electronically interleave the imaging and therapy ultrasound pulses generated by the transducers 50 to perform the imaging/therapy dual functions and/or to control motion (such as using one or more of motors 82, 84) of the transducer(s) 50 and/or probe module 42. In this manner, the master controller 110 may control an ultrasonic therapy dosing sequence that includes gated dose delivery based on detection of a suitable or acceptable path. In some implementations, the master controller 110, such as via module 114 may build and track anatomical context used to evaluate a path, such as when moving the imaging transducer(s) 52 within the probe module 42 or with respect to the patient's anatomy.

In the depicted example, an imaging module 44 is also depicted as being a component of the overall system. Such a module, if present, may control or monitor operation of transducers 50 (e.g., imaging transducers 52) to control generation, collection, and/or processing (e.g., reconstruction) of imaging data. In the depicted example, the imaging module 44 is also shown as being in communication with the master controller 110 of the therapy module 40, particularly with the image streamer and remote control sub-module 112, which may control operation of or respond to feedback and data from the imaging module 44. As with the probe module 42 and therapy module 40 discussed above, the imaging module 44 is illustrated as a separate module in FIG. 2 to facilitate illustration and explanation of the functional concepts. However, as with the preceding examples, the imaging module 44 may actually be one and the same with one or both of the probe module 42 and therapy module 40 (i.e., an integral structure or device configured to perform the combined functions of the imaging module and one or both of the therapy module and probe module as discussed herein).

With the preceding system description in mind and as context, the present techniques relate to an image (or unreconstructed image data) guided ultrasonic therapy system. In certain embodiments such a system may utilize separate imaging transducers 52 and therapy transducers 54. Alternatively, in other embodiments a single or combined transducer may be utilized for both the imaging and therapy ultrasonic energy applications. In embodiments where separate imaging transducers 52 and therapy transducers 54 are employed, the transducers may be optimized for their respective purpose and may be interleaved operationally by using the imaging transducers 52 to localize an internal anatomical target and the therapy transducers 54 to deliver an ultrasonic dose to the target once localized. This process may be repeated until an accumulated dose amount is attained.

Challenges with delivering accurate and safe ultrasonic therapy include poor acoustic coupling of the energy application device to the patient, "lift off" of a portion (e.g., an edge or corner) of the application device from the patient during treatment, the presence of an obstruction, such as an acoustic reflector or absorber (i.e. bones or ribs, gas filled cavities), in the therapy beam path, and/or the differences in acoustic properties around the targeted tissue causing aberrations in the path of the ultrasonic beam, hindering or preventing treatment. Such factors can result in delivery of an inaccurate dose amount and/or otherwise interfere with treatment or cause patient discomfort or unintended off-target effects. With this in mind, and as described herein, specific physical and algorithmic aspects of an ultrasonic therapy delivery system have been developed that may be employed to ensure a clear path (e.g., an absence of bone or bone-like structures, gas-filled pockets or cavities and so forth, good acoustic coupling, and no "lift off") for the therapy beam to propagate from the exit plane of the probe to the target region and beyond, thereby providing accurate dosing and patient safety. Further, such techniques may be employed by trained technicians or medical personnel performing ultrasound-based therapy or by untrained individuals, including the patient, performing ultrasound-based therapy, thereby allowing an untrained person to effectively deliver a prescribed dose to a target region without risk of injury.

By way of example, in one embodiment the imaging transducer(s) 52 and therapy transducer(s) 54 are arranged in an offset or standoff configuration, where the active area of the imaging beam is inclusive of the active area of the therapy beam at the point of penetration into the body (i.e., the interface formed by the skin surface and the exit plane of probe). Using this configuration, the challenges noted above can be mitigated via analysis of the ultrasound image data or reconstructed images. For example, poor coupling may manifest as unusually poor image quality or missing portions of the image, "lift off" often results in partially blacked-out portions of the image, and a bone in the therapy path is seen as a large reflector in the image that also blacks out the region behind it. Thus, in one implementation the probe is physically constructed so that the geometry of the therapy transducers 54 and the imaging transducers 52 ensures intersection of the imaging and therapy beams. Processor-executable routines are then employed in an automated manner to identify or otherwise detect some or all of the above problem indications in the ultrasound image (or raw image data) to ensure safe and accurate dosing. In some embodiments, one or both of the imaging transducers 52 or therapy transducers 54 may be moved (either by internal or external motion or motors), such as based upon signals or control routines generated by associated master control and image analysis routines to ensure a clear path. In other embodiments, simplified ultrasound pulse sequences or alternate sensor data is used to determine one or more of the criteria for the clear path determination.

With this in mind, a variety of example embodiments are described herein by which reconstructed images or raw image data may be utilized in conjunction with a therapy beam (e.g., an ultrasonic therapy beam) to apply a therapy or treatment, such as a neuromodulation therapy. The various example embodiments illustrate different imaging transducer 52 and therapy transducer 54 geometries and orientation, options for internal and external motion of the transducer assemblies, control schemes to ensure the imaging beam encompasses substantially or entirely the full acoustic window of the therapy beam, and algorithmic concepts to analyze the image data and/or sensor data to make clear path determinations.

Figure 3:
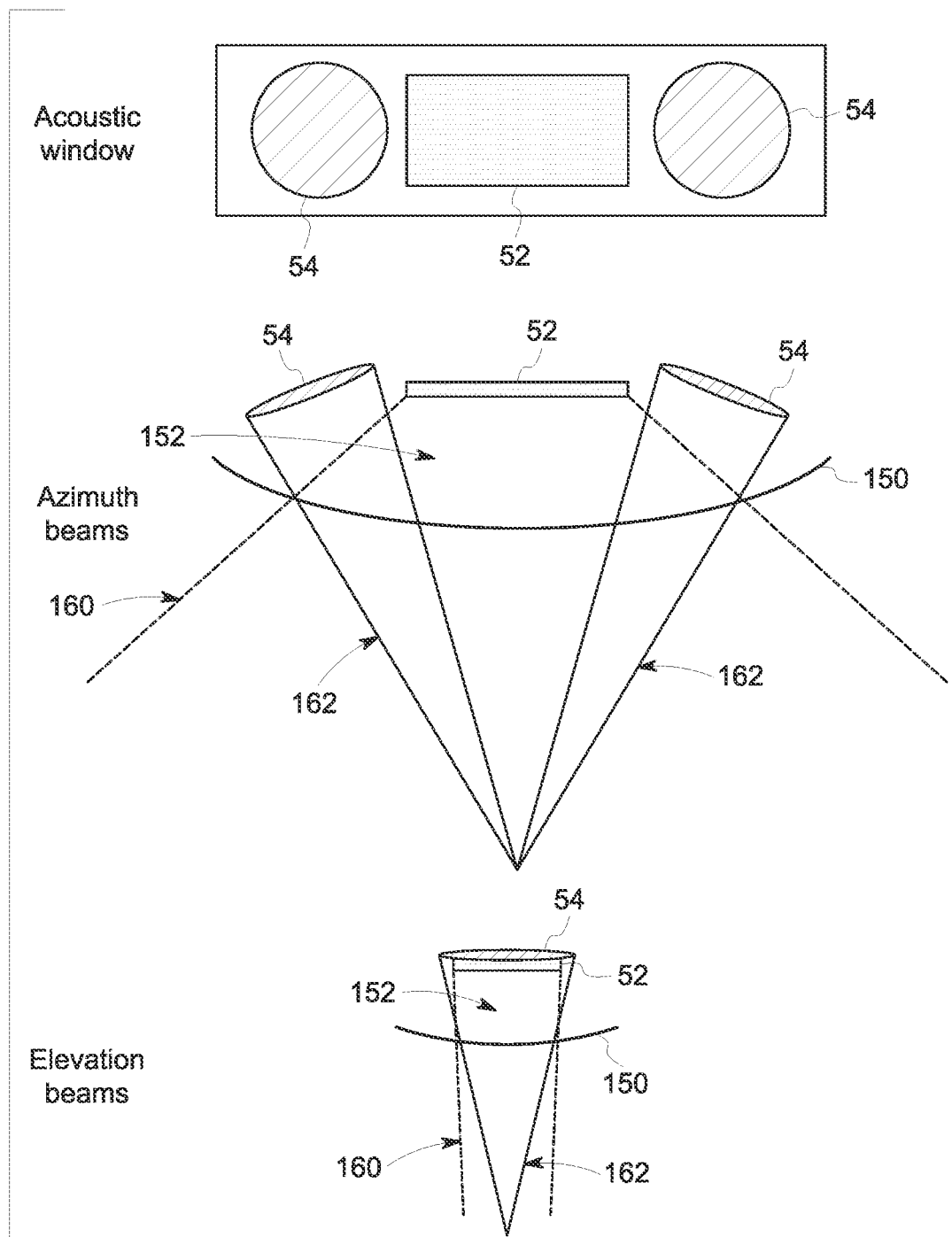
FIG. 3 depicts an embodiment of a static transducer arrangement for use in an ultrasonic probe, in accordance with aspects of the present disclosure.
Figure 4:
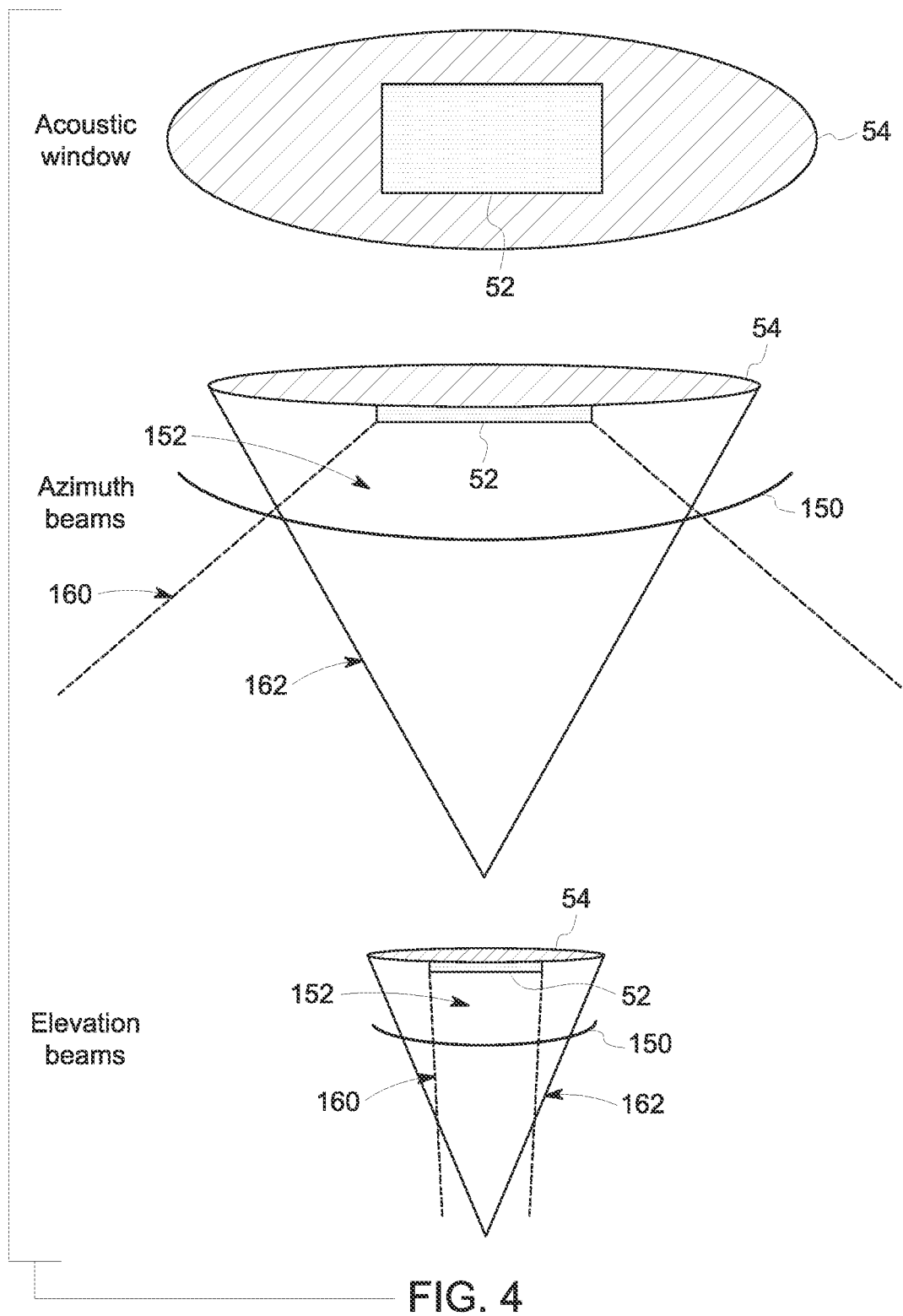
FIG. 4 depicts a further embodiment of a static transducer arrangement for use in an ultrasonic probe, in accordance with aspects of the present disclosure.
Figure 5:
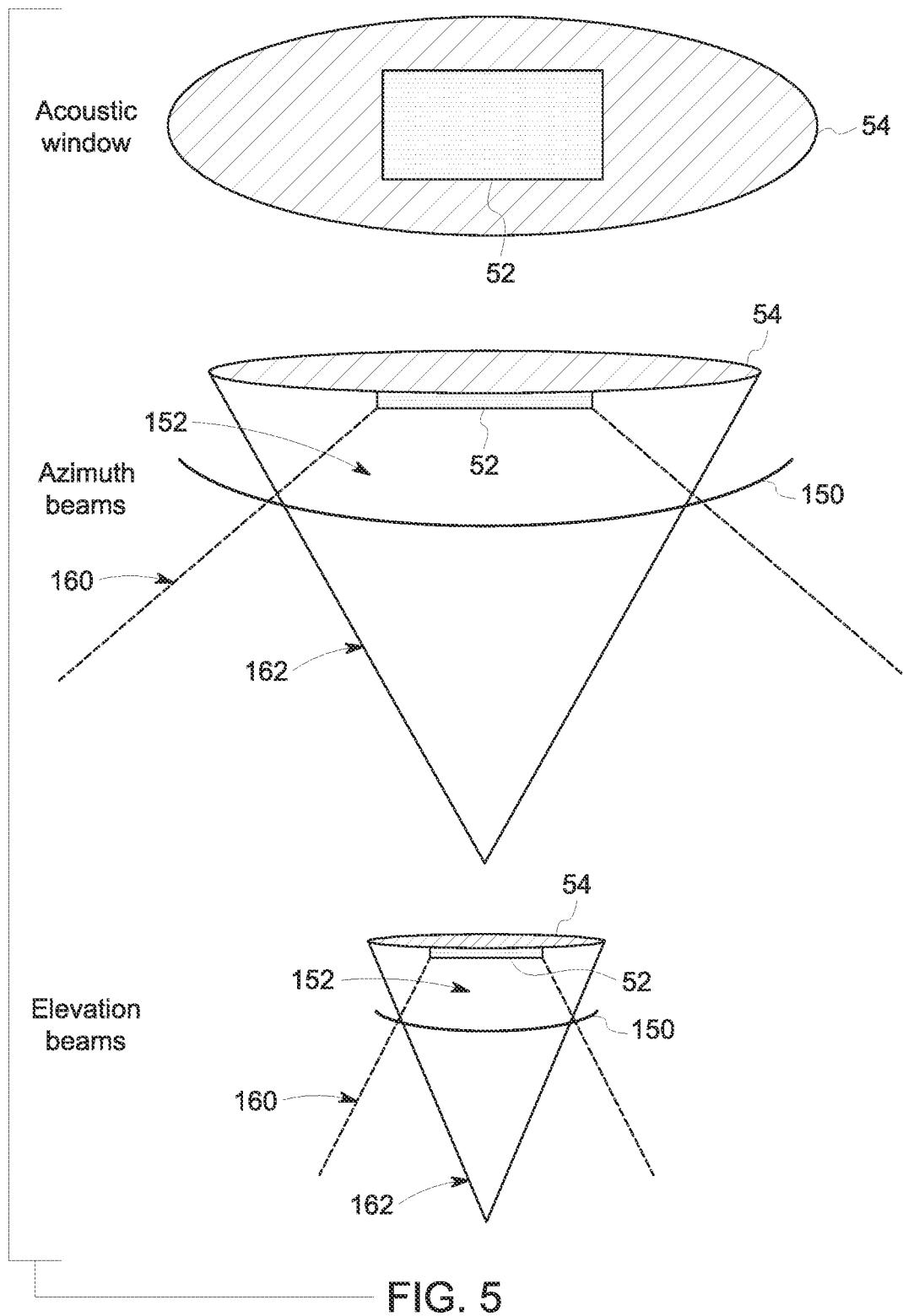
FIG. 5 depicts an additional embodiment of a static transducer arrangement for use in an ultrasonic probe, in accordance with aspects of the present disclosure.

A first set of embodiments may be characterized as static transducer configurations, examples of which are illustrated in FIGS. 3-5. In certain such implementations the image transducers 52 and therapy transducers 54 are in a probe that includes a cap 150 (e.g., a sonolucent cap) that is configured to contact the patient when in use. That is, the image transducers 52 and therapy transducers 54 are separated from the patient when in use by the cap 150 and an internal standoff 152 separating the transducers from the cap 150. The standoff 152 is sized or dimensioned to ensure coverage of the therapy beam path by the imaging beam at the patient interface onward in at least one dimension (i.e., blind spots are moved within the space encompassed by the cap 150). Due to the absence of motion of the transducer elements in a static configuration, the internal standoff 152 in these and other static transducer configurations may comprise a solid or a fluid material.

Examples of three such static transducer configurations are shown in FIGS. 3-5. In these three figures (and in subsequent configuration figures), three different views are presented that correspond to each respective configuration: (1) a top view corresponding to the acoustic window, (2) an azimuth view, and (3) an elevation view rotated 90° relative to the azimuth view.

In FIG. 3, a side-by-side transducer configuration is depicted in which an array of image transducers 52 is positioned in a linear side-by-side configuration with a pair of therapy transducer 54 arrays. In this example, the extent of the imaging beam 160 and of the therapy beam(s) 162 generated in this configuration is illustrated. As shown in this example, in this configuration there is overlap of the therapy beams 162 by the imaging beam 160 from the patient interface (i.e., the cap 150) outward due to the offset between the transducers 50 and the patient interface or contact location. That is, in the direction of propagation of the therapy beam 162 from the cap 150 into the body of the patient, the path traveled by the therapy beam 162 is fully encompassed within the imaging beam 160.

Turning to FIG. 4, a co-centric transducer configuration is illustrated that provides partial overlap of the therapy beam 162 by the imaging beam 160 from the patient interface (i.e., the cap 150) outward. In particular, as seen in the bottom elevation view, the therapy beam 162 is partially outside the extent of the imaging beam 160 near the skin surface (i.e., near the cap 150) but at greater depth is encompassed by the imaging beam 160. Such an approach may be suitable in contexts where the criteria for path determination or evaluation is relaxed to ensure that a substantial percentage (e.g., 70%) of the energy density of the therapy beam 162 is intersected at the skin surface by the imaging beam 160.

Turning to FIG. 5, an embodiment is depicted employing an electronic real-time three-dimensional (e4D) imager (e.g., array of image transducers 52) in which the e4D imager is capable of steering in the XY dimensions to fully intersect the therapy beam 162 within a series of sequential images. In the depicted example a co-centric transducer configuration is illustrated in which the e4D image transducer array is centrally positioned, though a side-by-side configuration is also suitable. Due to the steerability of the imaging beam 160, full coverage of the extent of the therapy beam 162 can be effectively obtained.

Figure 6:
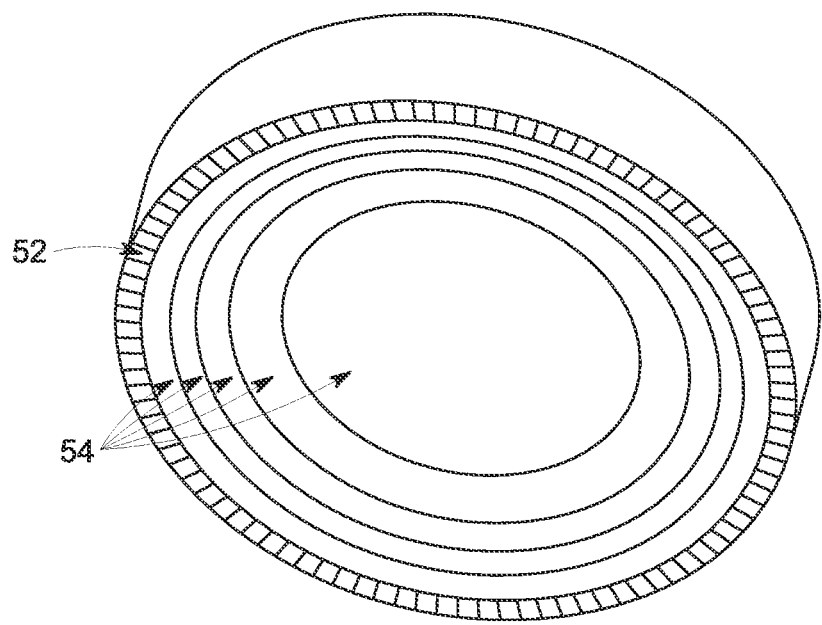
FIG. 6 depicts another embodiment of a static transducer arrangement for use in an ultrasonic probe, in accordance with aspects of the present disclosure.
Figure 7:
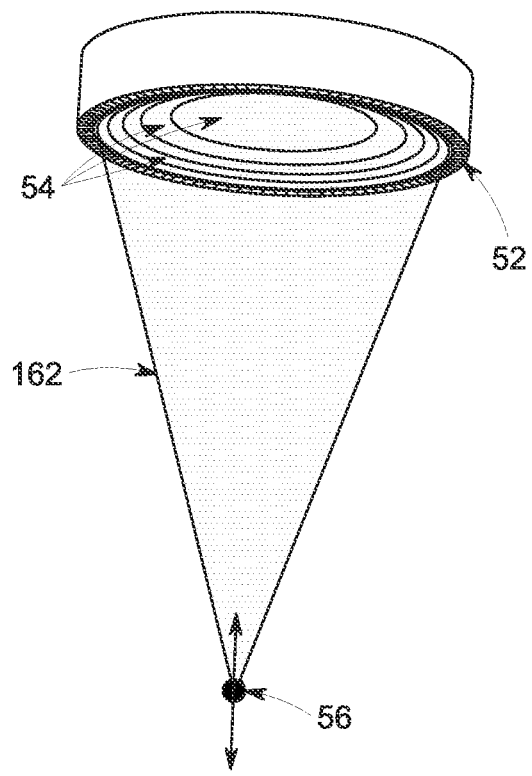
FIG. 7 depicts an example of the transducer arrangement of FIG. 6 emitting a focused therapy beam, in accordance with aspects of the present disclosure.
Figure 8:
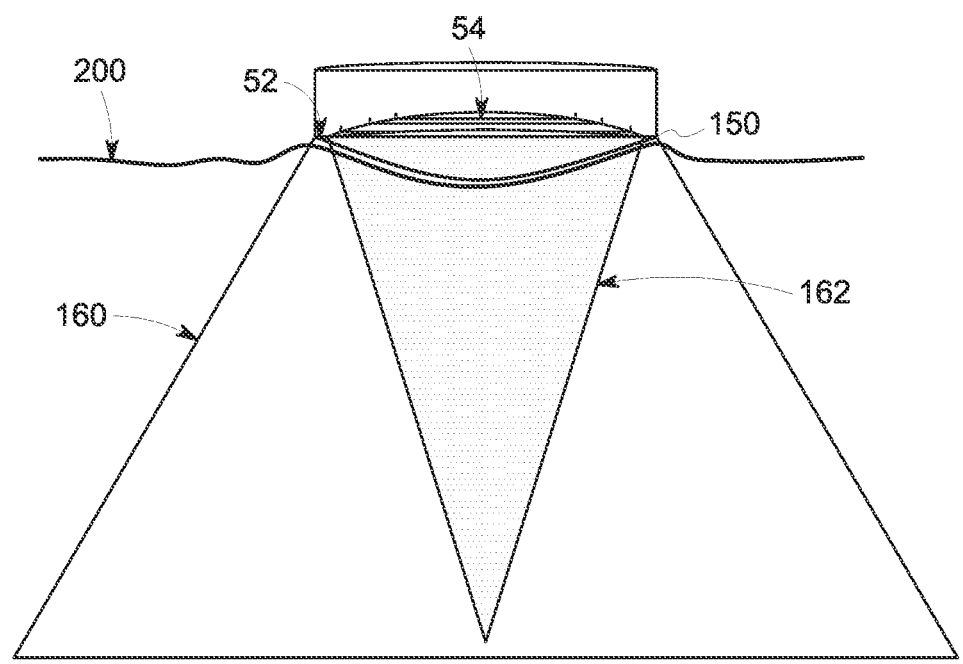
FIG. 8 depicts an example of the transducer arrangement of FIG. 6 emitting a focused therapy beam and an imaging beam encompassing the therapy beam, in accordance with aspects of the present disclosure.

With the preceding in mind, FIGS. 6-8 depict a further example of a static transducer embodiment, in this example, the image transducers 52 may be provided as one or more annular rings (i.e., as an annular imaging transducer array) along an outer perimeter of the probe face. In certain implementations, the array of image transducers 52 may be provided as a sparse 2D array that utilizes fewer channels compared to a fully sampled 2D array and which supports high quality volumetric imaging using techniques such as synthetic aperture beamforming. This perimeter imaging array facilitates verification of full contact between the probe 42 and the skin surface 200, as discussed herein. Within the annular imaging transducer array, a concave arrangement of annular and circular therapy transducers 54 are positioned (i.e., a multi-element therapy transducer array). This arrangement maximizes the active high intensity focused ultrasound (HIFU) aperture area and can be seen in the perspective view of FIG. 6.

In FIG. 7, this same arrangement is depicted, but with the therapy beam 162 generated by the therapy transducers 54 illustrated. In this depiction, a cone-shaped therapy beam 162 is shown focused on a focal spot 56 that may be used to target a target region. In one embodiment the therapy transducers 54 may be phased in order to allow for a variable or configurable focus depth, as shown by the movement arrows associated with the focal spot 56 in FIG. 7.

Both the therapy beam 162 and imaging beam 160 are shown together in FIG. 8 to provide further context and illustrate that the extent of the imaging beam 160 exceeds that of the therapy beam 162. Further, due to the annular image transducer array being positioned on the outer perimeter of the patient-contacting surface of the probe and due to the convex (i.e., dome shaped) patient contacting surface in the illustrated embodiment, probe "lift off" events may be detected using the image transducer array. That is, in the absence of full contact, a lift off artifact may be observed in the acquired image data, and an alert or therapy stoppage initiated.

Figure 9:
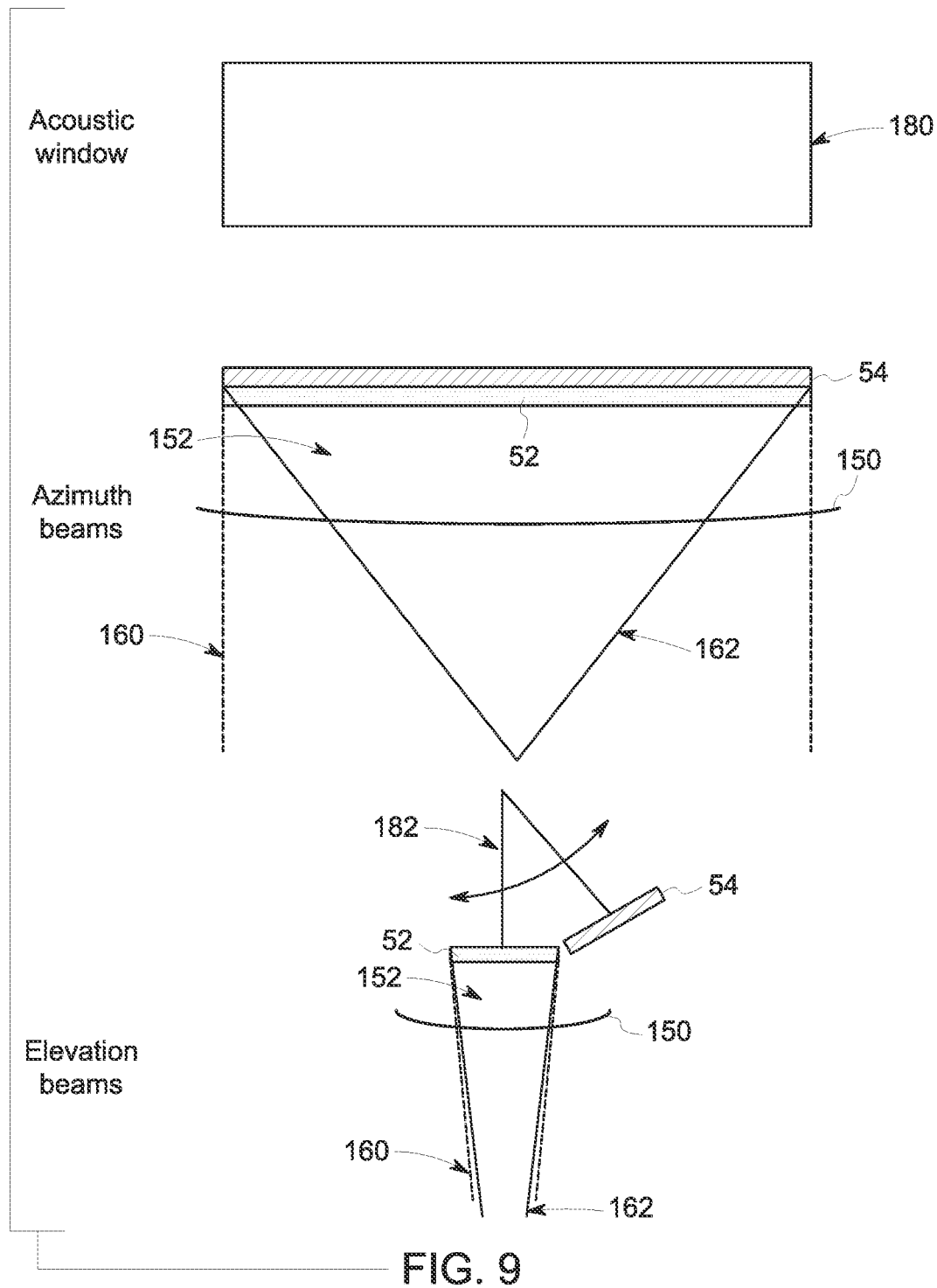
FIG. 9 depicts an embodiment of a dynamic transducer arrangement for use in an ultrasonic probe, in accordance with aspects of the present disclosure.
Figure 10:
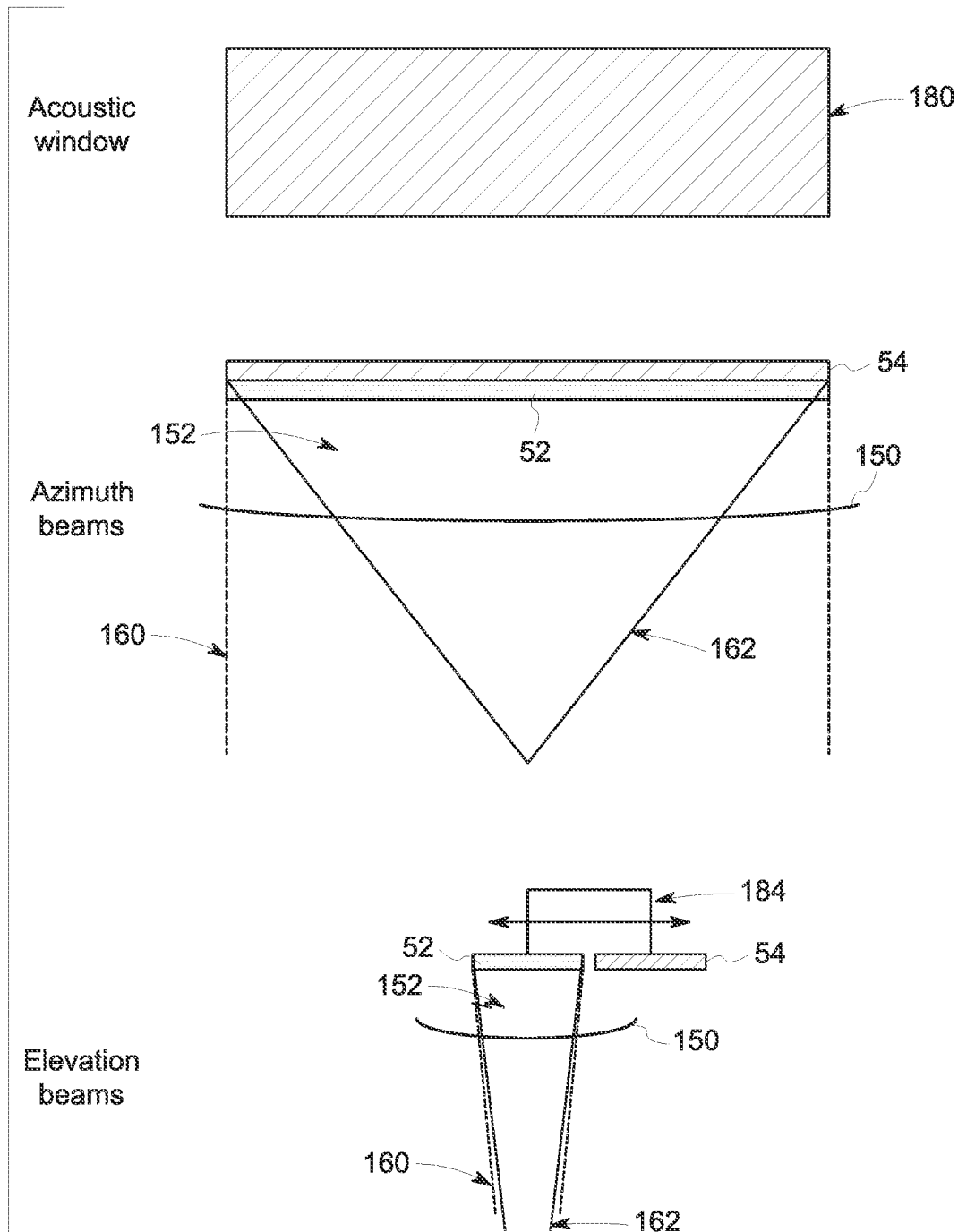
FIG. 10 depicts a further embodiment of a dynamic transducer arrangement for use in an ultrasonic probe, in accordance with aspects of the present disclosure.

While FIGS. 3-8 depict static transducer arrangements, other implementations are contemplated in which one or both of the image transducers 52 or therapy transducers 54 are moved during operation (i.e., dynamic transducer configurations). For instance, FIGS. 9-13 depict examples of what may be characterized as "dynamic" transducer configurations in which one or both of the image transducers 52 or therapy transducers 54 move during operation. By way of example, FIGS. 9 and 10 depict examples in which the image transducers 52 and therapy transducers 54 are provided as rectangular arrays (signified by rectangular acoustic window 180) that move in and out of position for operation. Due to the motion of the transducer elements, the internal standoff 152 in these and other dynamic transducer configurations may be fluid filled.

With this in mind, FIG. 9 depicts an example where the array of image transducers 52 and the array of therapy transducers 54 are alternately moved into operation position by an internal pendulum (having pendulum arms 182) so that the image transducers 52 and therapy transducers 54 are effectively rocked back-and-forth so that one set of transducers is in operating position (i.e., the acoustic window 180) when the other is not. Similarly, FIG. 10 depicts another embodiment where a linear or rotational motion stage is employed (signified by linear motion arms 184) to move the image transducers 52 and therapy transducers 54 between operational positions such that only one set of transducers is in an operational position (i.e., within the acoustic window 180) at a time. As shown in both embodiments, the image beam 160 fully encompasses the therapy beam 162 from both the azimuthal and elevation perspective.

Figure 11:
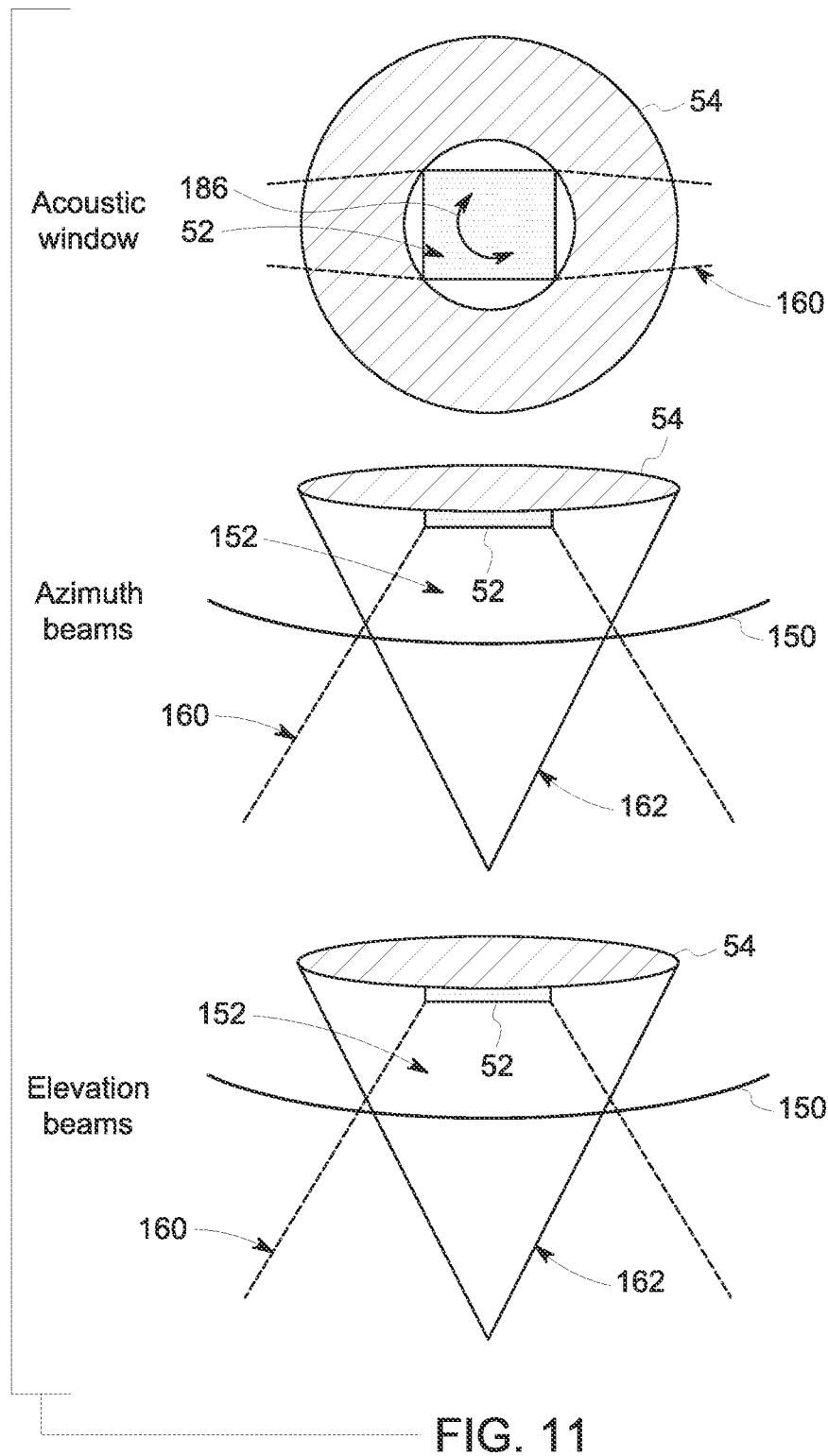
FIG. 11 depicts an additional embodiment of a dynamic transducer arrangement for use in an ultrasonic probe, in accordance with aspects of the present disclosure.

In FIG. 11 another dynamic transducer configuration is depicted. In this example the array of therapy transducers 54 is provided as a fixed annular array in which a rotatable array of image transducers 52 is positioned in the empty central region of the ring structure. The array of image transducers 52 in this example is configured to rotate at least partially about an axis so as to sweep the imaging beam 160 during operation to cover the full extent of the therapy beam 162 during an imaging sweep. By way of example, in one embodiment, the array of imaging transducers 52 may rotate or oscillate ±90° (depicted by motion arrows 186) about a central axis through the ring structure formed by the array of therapy transducers 54. In this manner, each sweep of the imaging beam 160 generated by the image transducers 52 encompasses the extent of the therapy beam 162 from both the azimuthal and elevation perspective.

Figure 12:
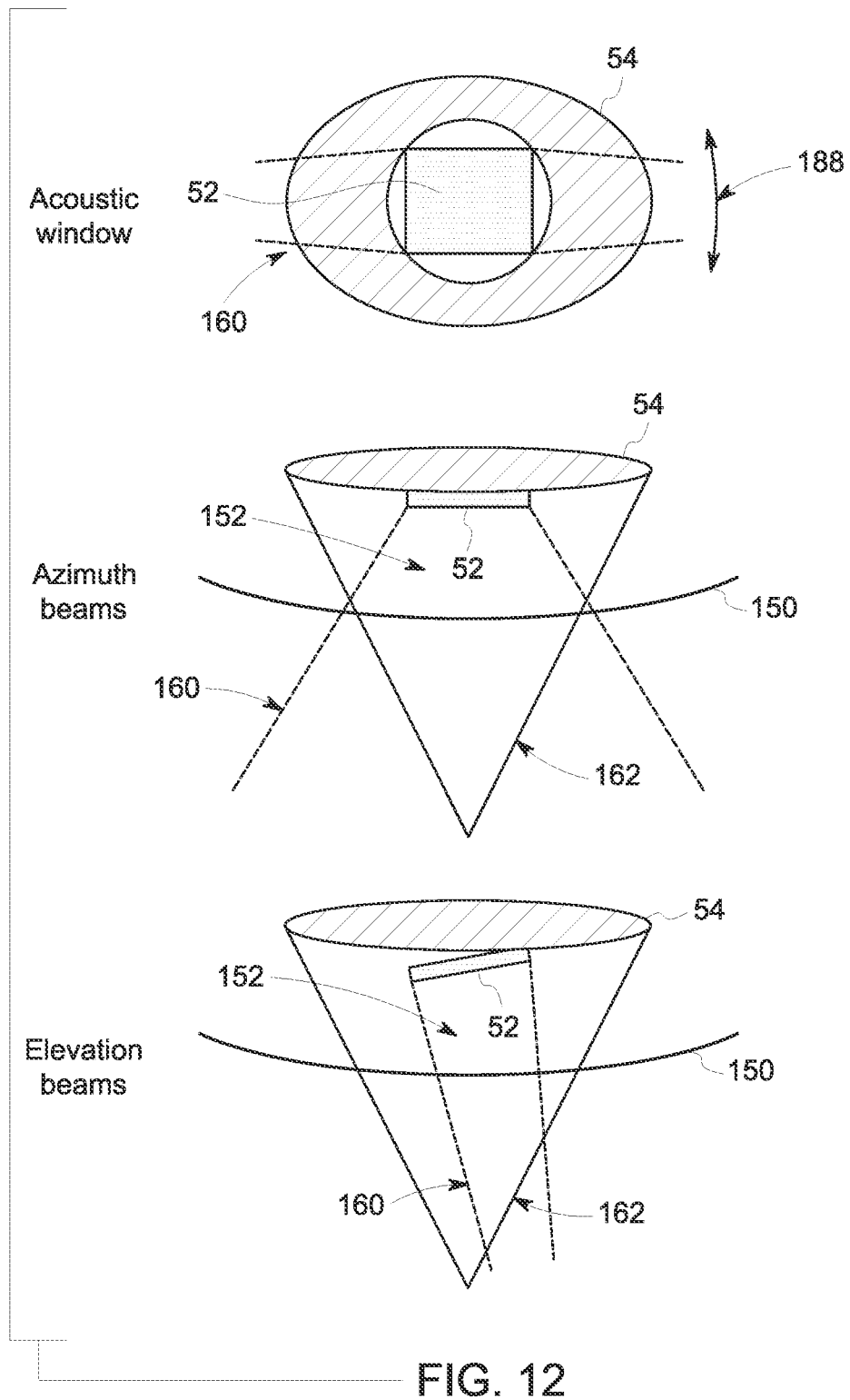
FIG. 12 depicts another embodiment of a dynamic transducer arrangement for use in an ultrasonic probe, in accordance with aspects of the present disclosure.
Figure 13:
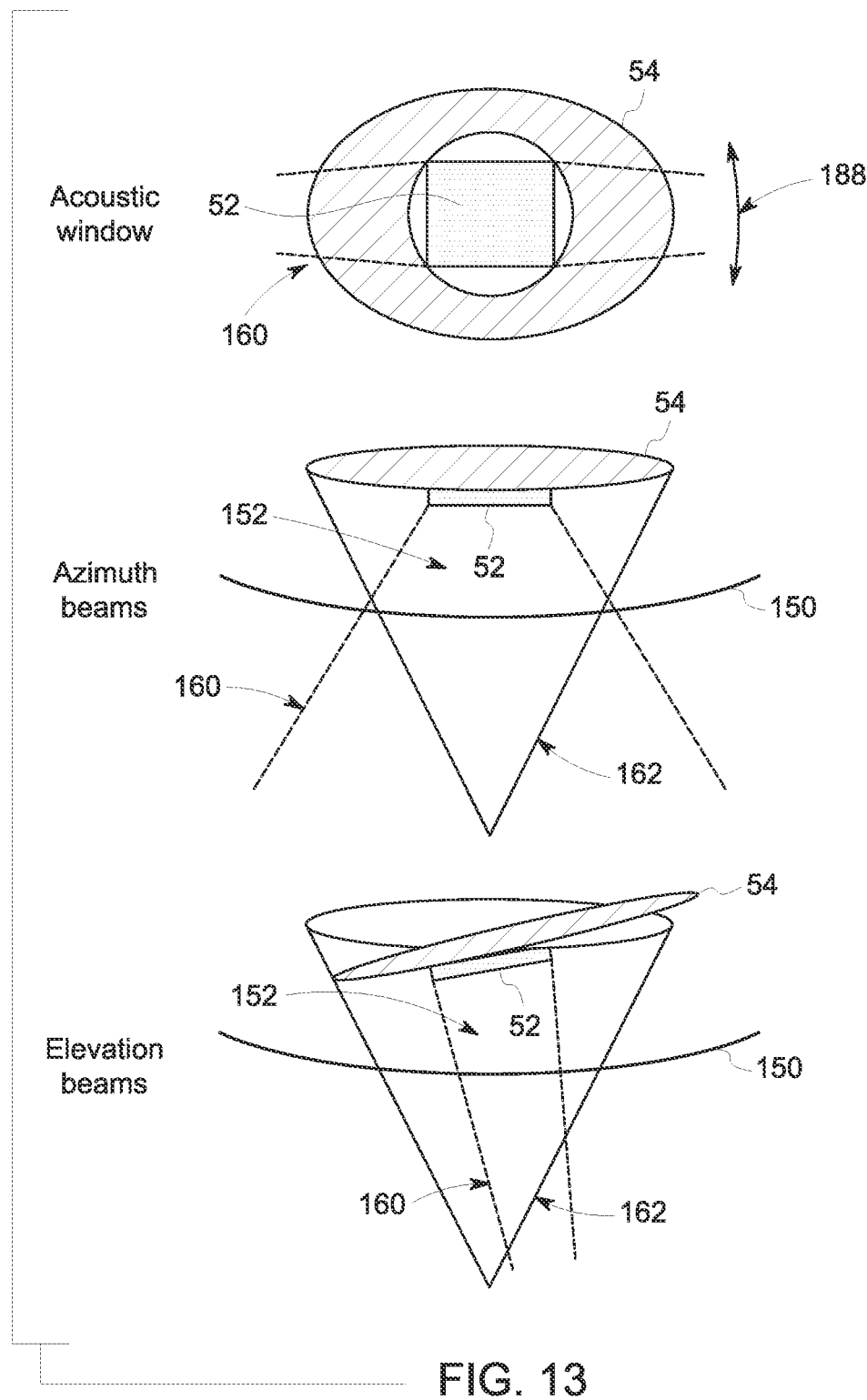
FIG. 13 depicts a further embodiment of a dynamic transducer arrangement for use in an ultrasonic probe, in accordance with aspects of the present disclosure.

In FIGS. 12 and 13 two further generally annular therapy transducer arrays are depicted for use in dynamic transducer configurations. In these examples the therapy transducer array structures are oval as opposed to circular (though circular array structures may instead be employed) but retain a central opening in which the array of image transducers 52 is positioned. In contrast to the example of FIG. 11, in which the array of image transducers 52 rotate within the plane defined by the annular array of therapy transducers 54, in these examples the array of image transducers 52 is tilted with respect to the planes formed by the therapy transducers 54 (depicted by motion arrows 188) so as to sweep in the elevation perspective during operation. The implementations of FIGS. 12 and 13 differ in whether the array of therapy transducers 54 tilts with the image transducer array (FIG. 13) or not (FIG. 12).

For example, turning to FIG. 12, in this implementation the array of therapy transducers 54 is fixed (i.e., does not rotate) relative to a central, tiltable array of image transducers 52 such that the imaging beam 160 can be tilted (i.e., swept) in the elevation dimension during operation. In this example, the maximum tilt angle allows the furthest extent at which the therapy beam 162 enters the patient to be seen by the imaging beam 160, as shown in FIG. 12. In this manner, the imaging beam 160 may be swept across the entire active area of the therapy beam 162.

In FIG. 13, a similar arrangement is illustrated, however the array of therapy transducers 54 and the array of image transducers 52 are fixed or bonded together so as to move (i.e., tilt) together in the elevation dimension. The concurrent tilt of the imaging beam 160 and therapy beam 162 allows the imaging beam 160 to view the entire acoustic window through which the therapy beam 162 will intersect. In this example, the maximum tilt angle allows the furthest extent at which the therapy beam 162 enters the patient to be seen, as shown in FIG. 13.

In a procedure in which this arrangement is employed the therapy beam 162 may be switched off while the transducers are jointly tilted so as to allow the path evaluation to be performed using the imaging beam 160. For example a controller or control circuit may sequence the motion (e.g., tilting) of the transducer arrays to facilitate path determination or analysis. Once the path is determined and/or confirmed to be acceptable, the controller or control circuit may re-center the transducer arrays and the therapy beam 162 may be turned on.

Figure 14:
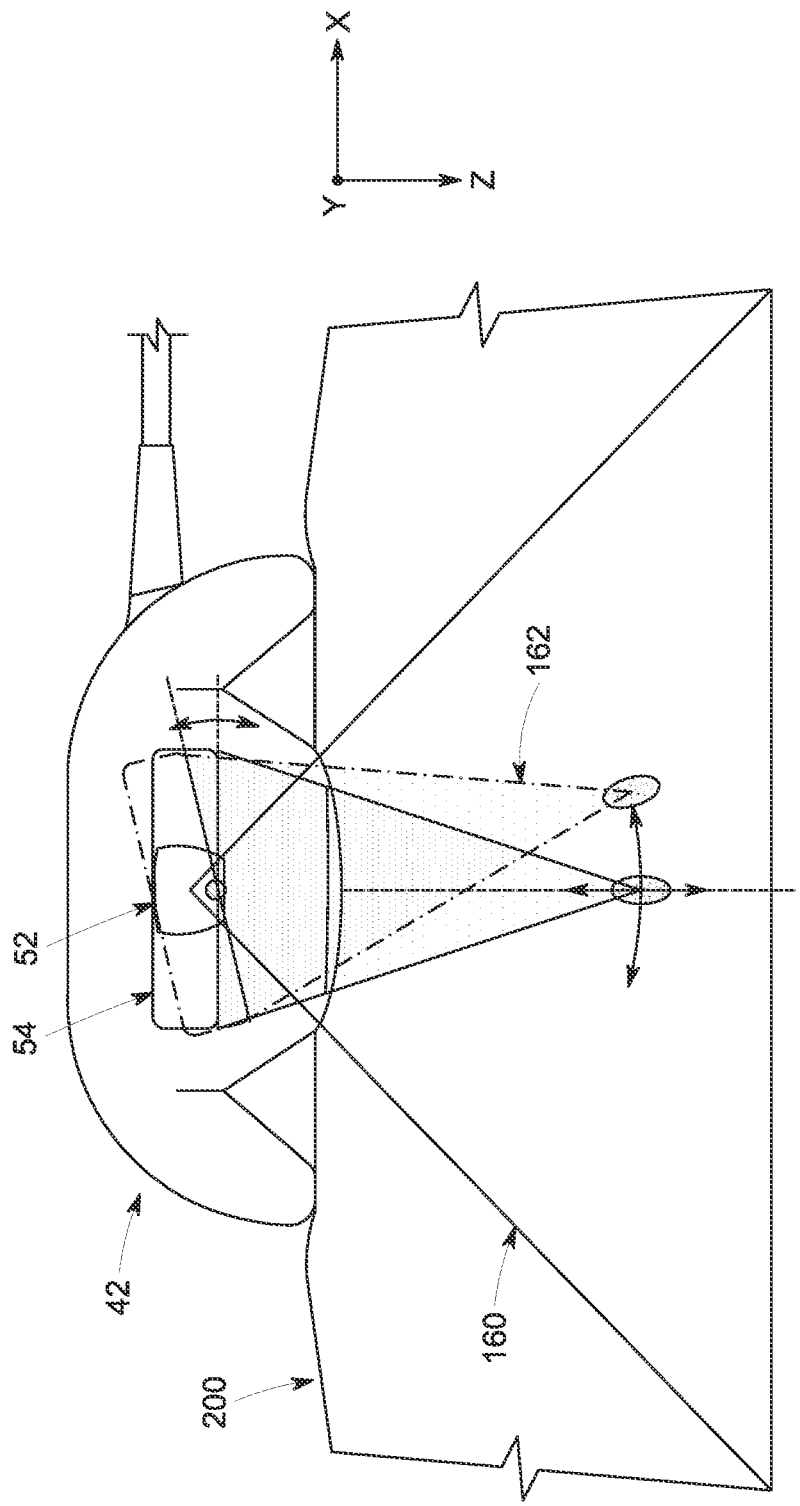
FIG. 14 depicts an additional embodiment of a dynamic transducer arrangement for use in an ultrasonic probe, in accordance with aspects of the present disclosure.

Turning to FIG. 14, a further dynamic embodiment is illustrated in a side sectional view. In this example, a body of the probe 42 is depicted which may be attached to the patient, such as by a belt or other attachment device, to secure or place the probe 42 on the patient at a treatment site. In the depicted embodiment, the therapy transducers 54 are moved (e.g., rocked) internally (i.e., within the probe) so as to cause movement of the therapy beam 162. The image transducers 52 are fixed in place however, and correspondingly the imaging beam 160 does not move. The imaging beam 160 however encompasses the extent of the range of motion of the therapy beam 162 when in use.

With this embodiment in mind, an example of the use of such a configuration may be provided. In this example the probe 42 may be coarsely aligned with the treatment site using a belt, harness, or other attachment mechanism, such as within ±2 cm in the X- and Y-dimensions. The field-of-view of the imaging beam 160 is broad enough to encompass the range-of-motion of the therapy beam 162. In one implementation the therapy transducers 54 are mechanically steered in the X-dimension over a range of ±15° and electronic focusing is employed in the Z-dimension over a range of ±4 cm. Such ranges of motion and focusing may be suitable to target a target region at a depth of 8 cm±4 cm. Such a configuration may be useful to allow coarse placement of the probe 42 with targeting and treatment logic to perform clear path determination and targeting of the target region using the imaging beam 160 and/or to allow automated movement and tracking of a target region that is subject to internal motion, such as due to respiration and/or cardiac movement.

Figure 15:
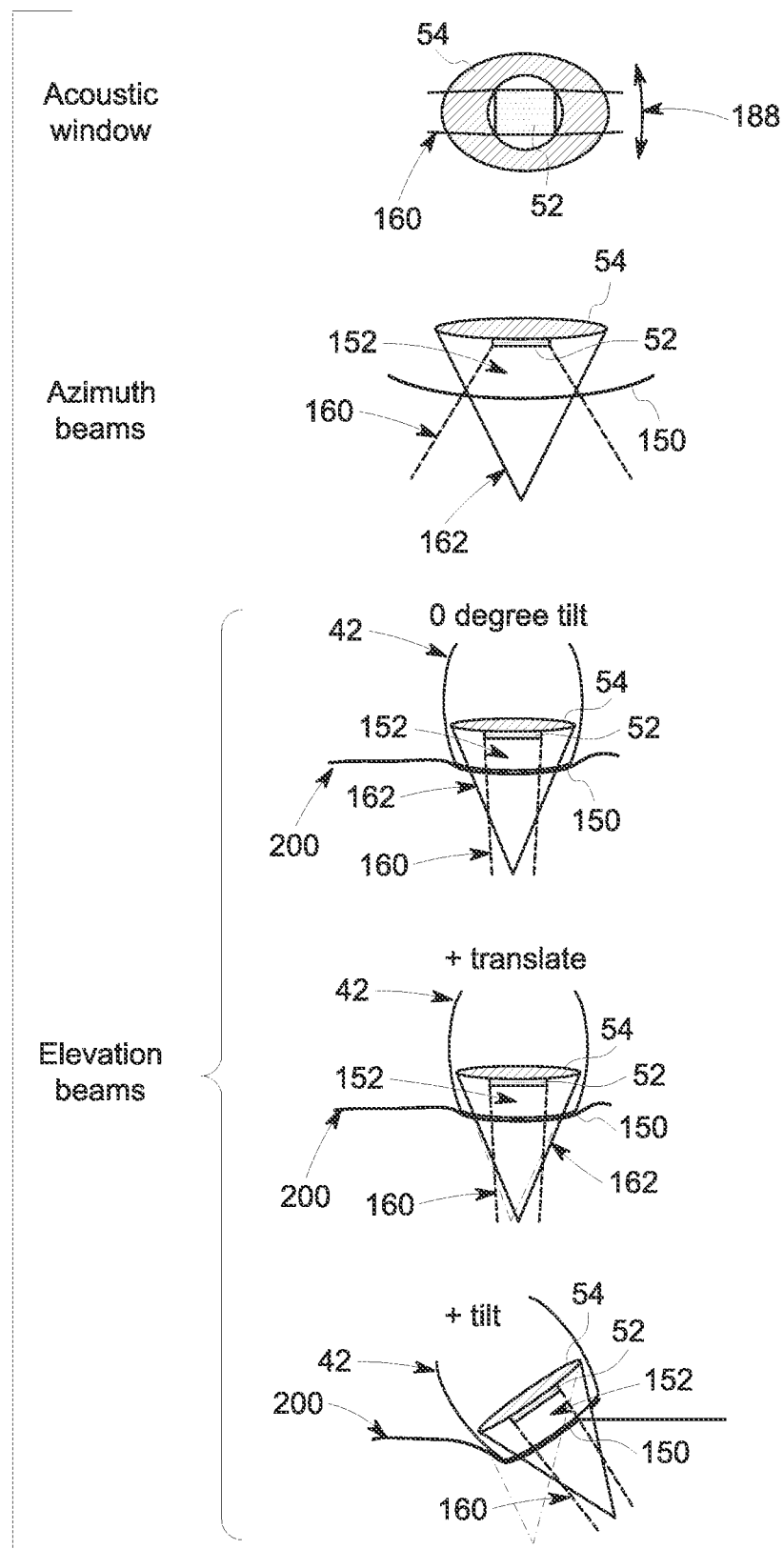
FIG. 15 depicts an embodiment of a transducer arrangement for use in an ultrasonic probe and subject to external motion, in accordance with aspects of the present disclosure.

The preceding embodiments utilize mechanisms internal to the probe 42 (e.g., motors, 82, 84) to cause motion within the probe 42 of one or both of the arrays of image transducers 52 or therapy transducers 54. The internal motion of the transducer array(s) is used to move or scan the imaging beam 160 over the target region through which the therapy beam 162 will pass. Turning to FIG. 15, in a further alternative the motion applied to the transducers may instead be an external force (i.e., movement caused by a force applied externally to the probe or probe body itself, as opposed to being applied internally to the transducer arrays), including user-guided manual motion or external motors provided on a mounting or attachment structure.

In FIG. 15, the structure depicted is similar to that illustrated in FIG. 13, however the array of image transducers 52 and therapy transducers 54 are fixed in place within the head of the probe 42. Instead the movement of the transducers 50 relative to the patient is accomplished by external movement of the probe 42. That is, the depicted example is effectively a static transducer structure subjected to dynamic external motion, which may be provided by external motors in a probe mount and/or by user-guided manual motion. In this example, in the elevation views, the image transducers 52 and therapy transducers 54 are shown in the context of the head or contact portion of a probe 42. The probe 42 may be moved, e.g., translated and/or tilted by application of external force or motion so as to sweep the image beam 160 relative to the potential treatment region under assessment for clear path considerations. By way of example, in one embodiment the probe 42 may be moved in one or more degrees-of-freedom with respect to the skin 200 of the patient to allow a path analysis or evaluation to be made prior to or during application of the therapy beam 162.

Figure 16:
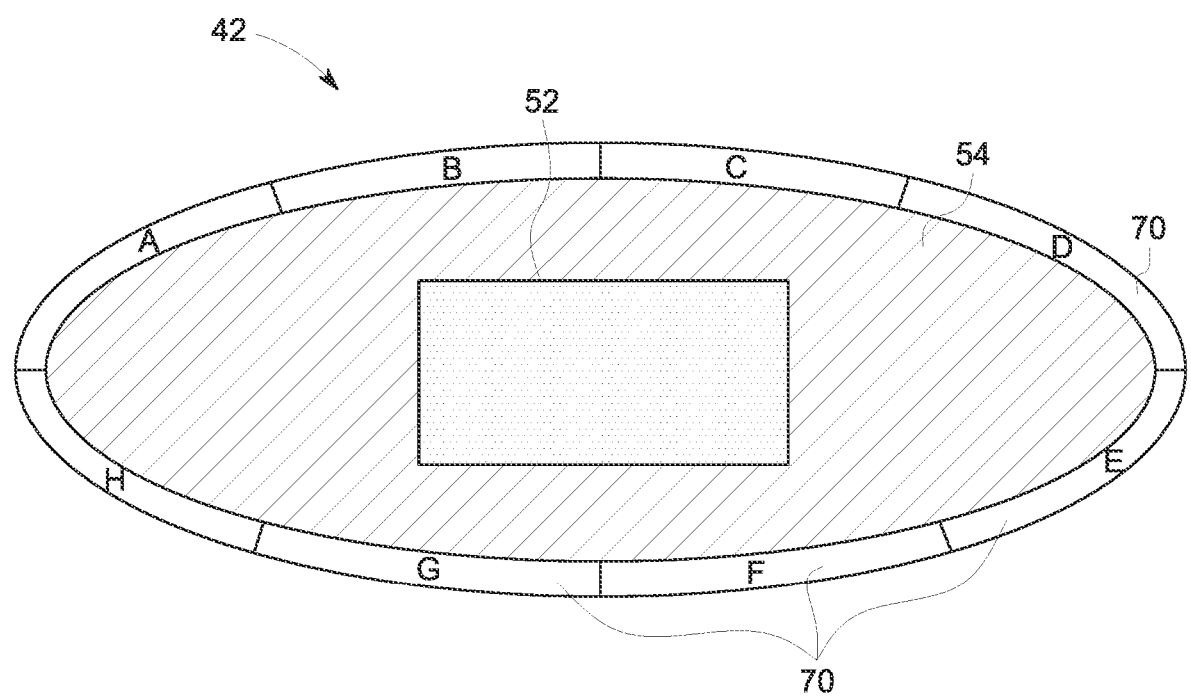
FIG. 16 depicts a view of an ultrasonic probe head that includes an arrangement of perimeter sensors, in accordance with aspects of the present disclosure.

The preceding discussion relates generally to the use of both image transducers 52 and therapy transducers 54 within an ultrasonic probe to provide an ultrasonic therapy. As noted, in certain embodiments other sensors or sensing arrangements may also be employed to better identify and address certain issues. With this in mind, and turning to FIG. 16, a patient-facing surface of an ultrasonic probe head is shown which includes sensors 70. In this example, co-centric image transducers 52 and therapy transducers 54 are illustrated in accordance with certain prior examples for the purpose of illustration, though the present discussion may also be relevant to other examples, as may be appreciated. Thus, the resulting imaging beam and therapy beam generated by the respective transducers may completely or partially overlap when in use. The depicted sensors 70 in this example are provided as a ring of sensors around the perimeter of the acoustic window.

In one embodiment some or all of the sensors 70 are electrodes and may be used to perform a "lift off" check and/or an acoustic coupling check. For example, in the context of a "lift off" check when the sensors 70 are electrodes, impedance of each electrode may be measured in an open circuit configuration, such as at system start-up. When the probe is contacted with the patient prior to administering a procedure, the impedance of each electrode may again be measured. A check (e.g., a one-to-one check) may then be performed on each electrode to determine that the impedance of each electrode has dropped significantly within the range or expected impedances for full-contact of the electrodes. That is, the initial impedance value of each electrode is compared to the post-contact impedance value of the respective electrode to confirm that the impedance drop exceeds a threshold value determined to be indicative of full-contact. The electrodes may also be checked or compared to confirm they have similar impedance values. Impedance value comparisons indicative of poor contact or "lift off" may result in an alert or indication to reposition the probe. Conversely, impedance value comparisons indicative of good contact and/or no "lift off" may result in the therapy being initiated or otherwise contribute to the evaluation of a present path of the therapy beam.

In another implementation where the sensors 70 are electrodes, an acoustic coupling check may be performed. In this example, when the probe is placed on the body of the patient before delivering therapy current may be sent from one electrode to another across the probe face (i.e., acoustic aperture). For example, a current excitation pattern may be employed such as: electrode A to electrode E, electrode B to electrode F, electrode C to electrode G, electrode D to electrode H, and so forth. For each current pattern, the measured impedance is compared to the range of expected impedances for full gel coupling across the entire acoustic aperture (i.e., the range of impedance values assuming good acoustic coupling and gel application across the aperture. If the degree of acoustic coupling is good, the current patterns will minimally penetrate the body, and will instead flow across the gel layer on the skin surface, which will result in low impedance values. Conversely, impedance values above a specified threshold may be indicative of poor acoustic coupling, requiring application of additional acoustic gel and/or repositioning of the probe. If the measured impedances are below the threshold however, acoustic coupling is acceptable and therapy can proceed.

In a further embodiment, the sensors 70 may instead be pressure sensors. In such an embodiment, the pressure sensors may be used to perform a "lift off" check. In such an embodiment, each pressure sensor may be initially calibrated or re-calibrated for a "no-contact" configuration, such as at system start-up. The contact force at each pressure sensor may then be measured when the probe is applied to the body of the patient prior to initiation of a treatment session.

A check (e.g., a one-to-one sensor check) may then be performed on each pressure sensor to confirm that the measured contact force when the probe is contacting the patient is indicative of full contact around the entire perimeter of the acoustic aperture. That is, the initial contact force of each pressure sensor is compared to the post-contact contact force of the respective pressure sensor to confirm that the measured contact force exceeds a threshold value determined to be indicative of full-contact around the perimeter. Contact force measurements indicative of poor contact or "lift off" may result in an alert or indication to reposition the probe. Conversely, contact force measurements indicative of good contact and/or no "lift off" may result in the therapy being initiated.

Figure 17:
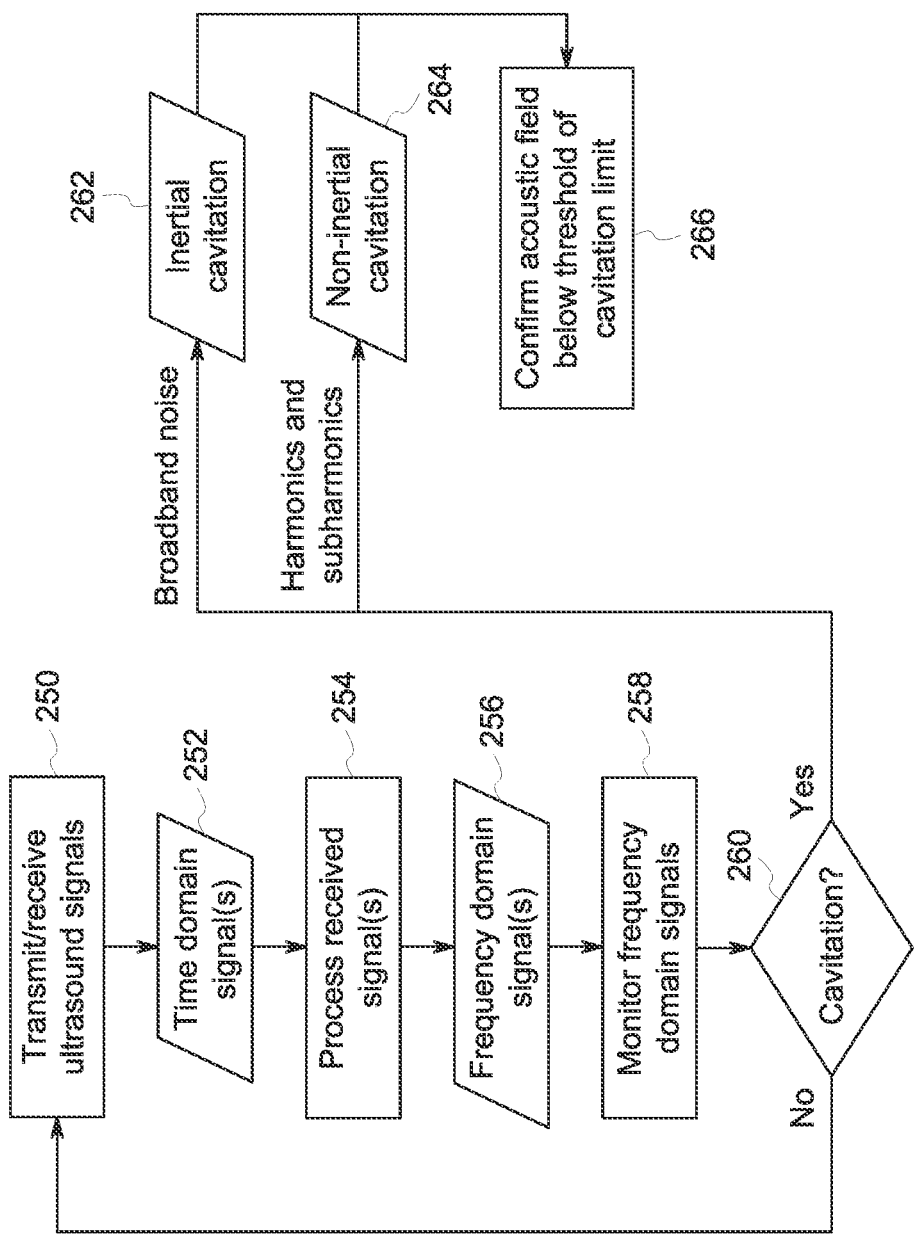
FIG. 17 depicts a process flow of steps in detecting a cavitation event, in accordance with aspects of the present disclosure.

In a further embodiment, the sensors 70 may instead be a passive cavitation detection sensor. In such an embodiment, the cavitation detection may be used to monitor the onset of acoustic cavitation to avoid tissue damage. Acoustic cavitation is the growth and collapse of pre-existing microbubbles under the influence of an ultrasonic field in liquids. There are two stages of cavitation: non-inertial cavitation and inertial cavitation. Non-inertial cavitation is the process in which small bubbles in a liquid are forced to oscillate in the presence of an acoustic field, when the intensity of the acoustic field is insufficient to cause total bubble collapse. Inertial cavitation is the process in which the bubbles collapse violently, driven by the inertia of the fluid. These two stages of cavitation can be detected by the cavitation detection sensor. Turning to FIG. 17, in such an embodiment, the cavitation sensor can be a single element ultrasound sensor or one channel of the imaging array with a selected/calibrated frequency range. The cavitation sensor can transmit/receive (step 250) a single-beam (A-line) ultrasound signal. The received A-line signal (e.g., time domain signals) 252 may then be processed (step 254). The signal processing procedures may include converting the time-domain signal 252 to frequency-domain signals 256 by performing Fourier Transform on the A-line signal. The frequency domain signals 256 may be monitored for appearance of harmonics, subharmonics, and broadband noise in the frequency-domain signals. The appearance of harmonics and subharmonics may indicate the onset of non-inertial cavitation 264. The appearance of broadband noise may indicate the onset of inertial cavitation 262. A check (e.g., a one-to-one sensor check) may then be performed on the cavitation detection sensor to confirm (step 266) that the acoustic field is below the threshold of cavitation limit and it is safe to perform therapy.

Figure 18:
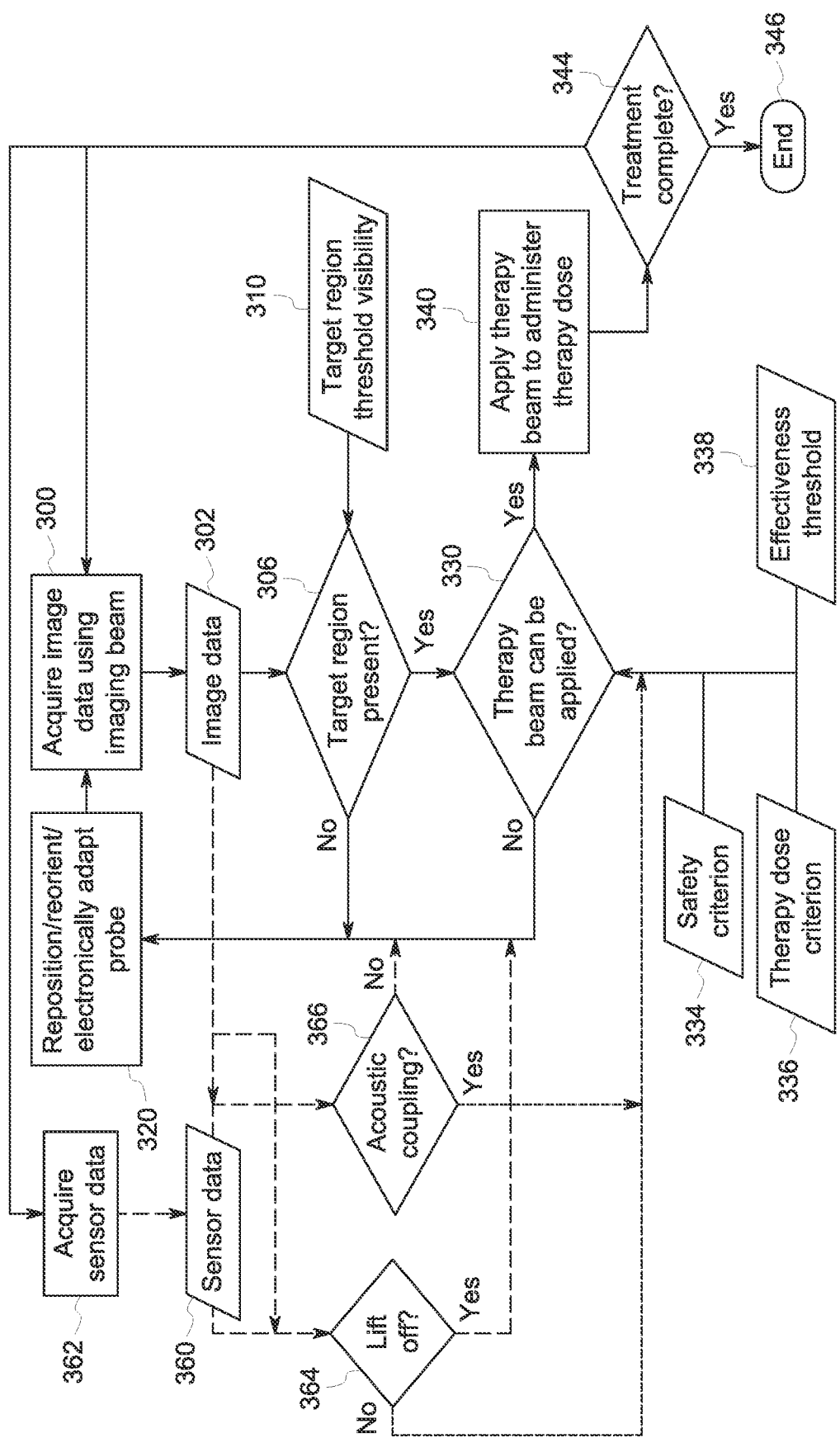
FIG. 18 depicts a process flow of steps in making a clear path determination and applying a therapy, in accordance with aspects of the present disclosure.

While the preceding relates various structural embodiments and examples of transducer configurations suitable for clear path determination, FIG. 18 depict a sample process flow depicting the steps in using certain of these embodiments. By way of example, FIG. 18 relates steps that may be suitable to perform image-based path evaluation and corresponding therapy delivery. Turning to the illustrated process flow, image data 302 is initially acquired (step 300) using the image transducers 52 (or combined transducers 50) of the respective probe structure 42. The image data 302 (either in the form of reconstructed images or as raw, unreconstructed data) may be analyzed to determine (decision block 306) whether all or part of the target region is visible or otherwise present in the image data. In practice, this determination 306 may be based on a threshold target region visibility 310 (e.g., percent visibility) that may be specified by a user, based on the treatment protocol, based on patient anatomy or demographics, and so forth. Further, in practice such a threshold visibility may be based on a raw percentage (e.g., 50% visible, 75% visible, 95% visible, and so forth), based on whether certain protocol specific features of the target region are visible, based on one or more of an effectiveness criteria that may be a function of percent visibility, range of therapy energy that can be applied, duration range over which the treatment protocol can be applied, certain features being of interest within the target region being visible and so forth. In this manner, the determination 306 is effectively determining whether the target region is present in the imaging beam 160 (which coincides substantially or entirely with the therapy beam 162) to a degree sufficient to activate the therapy beam 162 and perform a treatment session.

With reference to various real-world scenarios that may provide further context for such approaches, the spleen and liver provide two illustrative examples. With respect to the spleen, the effect of targeted ultrasonic-based therapy is generally homogeneous on the spleen tissue and, correspondingly, a lower percentage visibility (e.g., 50%) may be acceptable and may still yield the desired therapeutic effect. However, in order to target the spleen, the transducer will typically be positioned between the ribs, such that the ribs may be inadvertently within a proposed beam path. Further, the pancreas lies close to the spleen, also allowing for possible inadvertent overlap of targeted and non-targeted tissues. Correspondingly, a higher percentage of a safety criterion 334 (say 90%) may be employed for spleen-based therapies in conjunction with a lower visibility being tolerated.

Conversely, in the liver the effect of ultrasonic therapy is nonhomogeneous to the liver tissues. That is, particular regions, sub-regions, or anatomic structures or sub-structures of the liver (such as the porta hepatis) may need to be targeted to achieve the desired therapeutic effect. As a result, in contrast to the spleen example, a higher percentage visibility (e.g. 75%) may be specified in order to obtain the desired therapeutic effect. In addition, in contrast to the spleen example, for the liver, a lower safety criterion may be acceptable since access to the liver is epigastric (i.e., the transducer may be positioned on the skin of the soft tissue of the abdomen below the rib cage) which avoids bones and off-target energy would primarily land in the other lobes of the liver which have little therapeutic effects. This may allow for a lower or reduced safety criterion (e.g., a 75% safety criterion). Such a reduced safety criterion would not necessarily be indicative of an absence of safety concerns (since the stomach and intestines lie near the liver), however those safety concerns may be somewhat relaxed in view of the likely beam path (i.e., the probe position on abdomen and anatomy of the liver).

If the target region is not (or is not sufficiently) present in the imaged region, a remediating action 320 may be performed. Such remediating action 320 may include providing a notification to the user (e.g., the patient in certain examples) to reposition and/or reorient the probe structure 42. In response to the notification, a user may translate and/or tilt the probe head until a path including the target region and otherwise determined to be suitable is determined to exist. Alternatively, the remediating action may be automatically performed by the system, such as electronically adapting the probe performance (e.g., electronically sweeping the imaging and/or therapy beams to find a path to the target region, internally moving the transducer elements (in a dynamic transducer configuration as discussed herein) to find a path, or otherwise automatically adjusting position and/or operating parameters of the transducers 50 as discussed herein to achieve a path. For example, to the extent electronic beam steering is possible on the probe 42, the probe 42 may automatically sweep the scannable region using the embedded electronic motion control in an attempt to identify the target region and/or satisfy the path evaluation criteria.

In the event a path is determined to exist from the probe 42 to the target region, a further determination 330 may be made to ascertain whether other relevant factor or conditions are met for the path being evaluated. By way of example, as part of determination 330, factors related to safety criteria 334, therapy dose 336, and treatment effectiveness 338 for a path under evaluation may be considered. A determination that the therapy beam should not be applied due to one or more of these factors may result in the remediating action 320 being performed as discussed above.

In certain embodiments, the determination 330 may be based entirely or in part on analysis of the image data 302. The image data 302 may be analyzed using conventional approaches or by machine learning or artificial intelligence approaches. Such analysis may include identifying image or image data regions indicative of structures or regions (e.g., bone, cartilage, gas-filled cavities) of relatively high or low density relative to soft-tissue and that are present in the path to the target region. Such structures may be associated with acoustic absorption or reflection (e.g., shadowing) of ultrasonic energy in both the imaging analysis as well as therapy delivery. Adequacy of acoustic coupling between the patient and probe structure 42 may also be a factor in the determination 330, with poor acoustic coupling being determined based on regions or areas within the image data 302 that are overly blurry or dim relative to image data acquired under conditions of sufficient acoustic coupling. Analysis of image data 302 to determine a "lift off" condition in which a portion (e.g., an edge) of the probe 42 is not pressed against the skin of the patient and which may be indicated by no image or a dim image along an edge of the image data may also be performed.

If at decision block 330 it is determined that the therapy beam 162 can be applied, the transducers 50 (e.g., the therapy transducer(s) 52) may be activated to apply (step 340) the therapy beam 162 targeted to the target region. The therapy beam 162 may be applied to the target region over a time interval. Upon a determination that the therapy session is complete (decision block 344) (e.g., the prescribed therapy dose has accumulated at the target region), the therapy beam 162 may be turned off and the treatment ended (step 346). Conversely, if a set period of time has elapsed and the treatment is not completed, the path evaluation and transducer alignment may be repeated (such as after repositioning of the probe 42) until the treatment is completed. It should also be appreciated that, while one sequence of steps is depicted with respect to FIG. 18, in practice certain of the steps may be performed in a different order.

In a further aspect of the present techniques, therapy transducers and control schemes may be employed that allow the selective activation and deactivation of respective subsets of the therapy transducers 54 based on the results of the path analysis or evaluation. By way of example, based on the path analysis, a subset of therapy transducers 54 having a clear path to the target region may be selected for activation while, correspondingly, a different subset of therapy transducers 54 lacking a clear path based upon the path analysis may be selectively deactivated for a given treatment administration. In such an embodiment, with respect to the process flow illustrated in FIG. 18, a path analysis determination at one or both of decision blocks 306 and 330 may be qualified or partial, i.e., a clear path may be determined to exist for a portion of the therapy transducers 54, but not all of the therapy transducers 54. In this implementation, instead of requesting the user reposition and/or reorient the probe, a threshold quantity or percentage (e.g., 50%, 75%, 85%, 95%, and so forth) of therapy transducers 54 may be determined to have a clear path and the therapy may be administered by activating only therapy transducers 54 having a clear path. Further, in such a scenario computer-implemented routines or control schemes may be employed to dynamically adjust the intensity and/or duration of the activated subset of therapy transducers 54 to optimize treatment administration for a given position and/or orientation of the probe 42. In such a context, repositioning and/or reorientation of the probe 42 may be reduced or eliminated due to dynamic adjustments made to the activation of and/or operating parameters of the therapy transducers 54.

As discussed herein, in practice certain of these considerations may also utilize sensor data 360 acquired (step 362) using one or more sensors 70 provided internal or external to the probe 42, such as electrodes, cavitation sensors, pressure sensor, and so forth. Such sensor data 360 may be utilized in addition to or instead of image data 302 for the purpose of evaluating certain factors that may be considered in determining whether to proceed with therapy beam application. Further in some implementations a signal generated by individual elements of the therapy transducer array (i.e., therapy transducers 54) may be used as part of the path determination, such as to identify large reflections or other signatures in the echo that are indicative of a blocking anatomy, to determine sufficiency of acoustic coupling, and so forth. In the depicted example, sensor data 360 may be used in addition to or instead of image data 302 to determine (step 364) the presence or absence of a probe head "lift off" event, the result of which may be a factor considered at decision block 330. Similarly, the same or different sensor data 360 may be used in addition to or instead of image data 302 to determine (step 366) the sufficiency of acoustic coupling between the probe head and the patient, the result of which may be a factor considered at decision block 330.

The preceding discussion relates various devices, transducer configurations, and methodologies and steps that may be utilized to analyze or evaluate a therapy beam path in a patient therapy context and to use such a determination to deliver a prescribed ultrasonic dose to a target region of the patient in a safe manner. Indeed, use of the path evaluation techniques as discussed herein may allow safe application of ultrasonic therapy by a person otherwise untrained to apply such a dose, including individuals with little or no medical training or even the patient themselves. By ensuring there is a clear path at the point of entry and along the propagation path of the therapy beam 162, there is no need to impose detrimental transducer design constraints (e.g., coherent imaging and therapy frequencies, which would require compromises in imaging and therapy performance). There is also no need for elaborate controls and algorithms that quantify therapy delivery by visualizing the therapy beam and mitigate corruption of the image while simultaneously imaging and delivering therapy. These advantages allow for a purpose-built, low-cost system for imaging and therapy.

Further, with respect to alternatives, for other approaches to provide comparable functionality they would need to quantify the therapy beam at the target region through some other means than what is described herein. In a strictly ultrasound-based system, this would likely involve visualizing the therapy beam in the image, or other advanced signal processing techniques that measure actual ultrasound energy deep within the body. The present approaches work without having such visualization or measurement requirements.

In particular, while it is may be appealing to quantify the true dose, this is difficult in practice and involves additional requirements that might make many aspects of the combined imaging/therapy system difficult, large, and expensive. For example, to visualize the beam, coherent imaging and therapy frequencies may be employed. This involves a compromise where the imaging frequency is lower than desired (reduced resolution), and the therapy frequency is higher than desired (increased attenuation reduces therapy power to levels that are likely ineffective). This results in sub-optimal imaging and therapy performance with this approach and would require the development of new wideband transducer materials. Further, to visualize the therapy beam, simultaneous imaging and therapy ultrasound signals are applied. In such an arrangement the therapy ultrasound signal will corrupt the image, target localization more difficult. Further, when using other advanced signal processing techniques instead, very high imaging resolution is required, which requires the use of a system of similar complexity to large console systems. Such a system is impractical for use at home or by untrained individuals, in contrast to the present approaches.

The disclosed techniques permit delivery of ultrasonic therapy energy (e.g., neuromodulating energy) to a target region in conjunction with a clear path determination that may assess one or more of: (1) presence of non-soft tissue regions within the therapy beam path (e.g., bone or bone-like structures, gas-filled cavities, and so forth), (2) partial "lift-off" of the probe head; or (3) sufficiency of acoustic coupling. Upon determination or confirmation of a clear path with respect to some or all of these factors, the therapy beam may be delivered to the target region.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A neuromodulation system, comprising:
   an ultrasound energy application device configured to deliver a neuromodulating energy dose to a target region in a subject; and,
   a controller configured to:
   receive real-time ultrasound image data of an internal tissue of the subject, wherein the ultrasound image data depicts anatomical structures when reconstructed;
   identify the target region in the internal tissue of the subject based on the ultrasound image data;
   identify an obstructive anatomical region based on anatomical structures depicted within the ultrasound image data;
   generate a path analysis of the ultrasound energy application device based on the target region and the obstructive anatomical region identified in the ultrasound image data, wherein the path analysis comprises identifying a clear beam path for a first subset of one or more elements of a therapy transducer array of the ultrasound energy application device based on the identified target region and an obstructed beam path for a second subset of the one or more elements of the therapy transducer array based on the identified obstructive anatomical region positioned between the second subset and the target region;
   determine a clearance metric of the clear beam path for delivering the neuromodulating energy dose along the clear beam path and using the first subset of the one or more elements;
   compare the clearance metric to an effectiveness threshold to determine if the clear beam path is sufficient for delivering the neuromodulating energy dose along the clear beam path;
   dynamically adjusting a duration of treatment based on the clearance metric, wherein the clearance metric corresponds to a percent visibility of the target region in the image data; and
   initiating delivery of the neuromodulating energy dose to the target region for the adjusted duration, wherein initiating delivery of the neuromodulating energy dose comprises activating only the first subset of the one or more elements of the transducer array of the ultrasound energy application device and not the second subset based on identification of the obstructive anatomical region.

2. The system of claim 1, wherein the ultrasound energy application device further comprises:
   a sonolucent cap configured to contact a skin surface of the subject; and
   a standoff region positioned between the sonolucent cap and at least a portion of one or more of the elements of the transducer array of the ultrasound energy application device, wherein the sonolucent cap and the standoff region hold the one or more elements in a fixed position relative to the skin surface when in use and wherein the one or more elements are separated from the sonolucent cap via the standoff region.

3. The system of claim 1, wherein determining the clearance metric comprises:
   determining whether one or more of a therapy dose criterion, beam characteristic, or an off-target safety criterion is met by the clear beam path based on a presence of the obstructive anatomical region determined based on the ultrasound image data and the activation of only the first subset.

4. The system of claim 1, further comprising one or more sensors configured to generate sensor data, wherein the one or more sensors comprise one or more of electrodes, pressure sensors, or passive cavitation detection sensors.

5. The system of claim 4, wherein determining if the clear beam path is sufficient for delivering the neuromodulating energy dose along the clear beam path comprises:
   determining, using the ultrasound image data or sensor data, sufficiency of acoustic coupling of the ultrasound energy application device to the subject.

6. The system of claim 4, wherein determining if the clear beam path is sufficient for delivering the neuromodulating energy dose along the clear beam path comprises:
   determining, using the ultrasound image data or sensor data, presence of a lift-off event of the energy application device with respect to the subject.

7. The system of claim 6, wherein initiating delivery of the neuromodulating energy dose comprises activating the first subset of the one or more elements of the transducer array of the ultrasound energy application device based on the presence of a lift-off event of the energy application device with respect to the subject.

8. The system of claim 1, wherein the one or more elements of the therapy transducer array emit the neuromodulating energy dose within a first frequency range and one or more elements of an imaging transducer array separate from the therapy transducer array emit an imaging beam used to acquire the real-time ultrasound image data within a second frequency range that is higher than the first frequency range.

9. The system of claim 1, wherein the controller is configured to perform further actions comprising:
   generating a notification or message to perform one or more of repositioning or reorienting the ultrasound energy application device in response to a determination that a sufficient portion of the target region is not present in the ultrasound image data or a determination that the clear beam path is not sufficient based on a comparison to the effectiveness threshold;

repeating the determination whether the target region is present in the ultrasound image data and the determination whether the clear beam path is sufficient based on the comparison to the effectiveness threshold; and controlling application of a therapy beam to the target region based on both determinations having a positive result to initiate delivery of the neuromodulating energy dose based on the positive result of both determinations.

10. The system of claim 1, wherein the controller is configured to perform further actions comprising:

automatically adjusting one or both of a position or orientation of the one or more elements in response to a determination that a sufficient portion of the target region is not present in the ultrasound image data or a determination that the clear beam path is not sufficient based on a comparison to the effectiveness threshold; and repeating the determination whether the target region is present in the ultrasound image data and the determination whether the clear beam path is sufficient based on the comparison to the effectiveness threshold until both determinations have a positive result and initiating delivery of the neuromodulating energy dose based on the positive result of both determinations.

11. The system of claim 2, wherein the ultrasound imaging data is generated from an imaging beam, the imaging beam fully encompassing an extent of a therapy beam of the neuromodulating energy dose in at least one dimension past the sonolucent cap.

12. The system of claim 1, wherein determining the clearance metric of the clear beam path comprises identifying anatomical structures associated with acoustic reflection or absorption in the clear beam path.

13. The system of claim 1, wherein determining the clearance metric of the clear beam path comprises identifying anatomical structures of different density than the target region in the clear beam path.

14. The system of claim 1, wherein the effectiveness threshold is based on an effective neuromodulating energy dose associated with a targeted physiological outcome.

15. The system of claim 1, wherein the controller is configured to dynamically adjust one or both of an intensity or duration of energy delivered while applying the neuromodulating energy dose based on the determined clearance metric.

16. The system of claim 1, wherein a static transducer configuration of the ultrasound energy application device comprises:

a co-centric transducer, further comprising:

an imaging transducer array, wherein the imaging transducer array comprises an electronic real-time three-dimensional imager (e4D) and the therapy transducer array.

17. The system of claim 1, wherein a dynamic transducer configuration of the ultrasound energy application device comprises:

the therapy transducer array, wherein the therapy transducer array is configured as a fixed annular array; and a rotatable array of imaging transducers, wherein the rotatable array of imaging transducers is positioned within a central region of the therapy transducer array and can rotate or oscillate.

18. A neuromodulation method, the method comprising:

acquiring ultrasound image data of a subject using an ultrasonic imaging beam of an energy application device, wherein the ultrasound image data depicts anatomical structures when reconstructed;

identifying an obstructive anatomical region based on anatomical structures depicted within the ultrasound image data;

determining, based on the ultrasound image data, that a sufficient portion of a target region for therapy is present in the ultrasound image data, wherein the target region is partially obstructed by the obstructive anatomical region;

in response to determining that a sufficient portion of the target region is present in the ultrasound image data, determining whether a neuromodulating energy dose can be applied to the target region via the energy application device, wherein a path of an ultrasonic therapy beam of the neuromodulating energy dose at least partially overlaps a path of the ultrasonic imaging beam within the subject;

dynamically adjusting a duration of treatment based on a clearance metric, wherein the clearance metric corresponds to a percent visibility of the target region in the image data; and in response to determining that the neuromodulating energy dose can be applied to the target region, activating only a subset of elements of a therapy transducer array to emit the neuromodulating energy dose to the target region for the adjusted duration of the subject, wherein the activated subset is associated with a clear path to the target region not obstructed by the obstructive anatomical region and an inactivated subset of the elements is associated with an obstructed path to the target region.

19. The method of claim 18, wherein determining whether the neuromodulating energy dose can be applied to the target region further comprises:

identifying within the ultrasound image data off-target anatomical structures that are within the path of the neuromodulating energy dose as part of identifying the obstructed path and the clear path; and determining whether one or more of a therapy dose criterion, beam characteristic, or an off-target safety criterion is met by the path based on a presence of identified off-target anatomical structures.

20. The method of claim 18, wherein determining whether the neuromodulating energy dose can be applied to the target region comprises:

comparing a portion of the target region that would be modulated by the neuromodulating energy dose with an effectiveness threshold.

21. The method of claim 18, wherein activating the subset of elements of the transducer array to emit the neuromodulating energy dose is further based on a sufficiency of acoustic coupling of the energy application device to the subject.

22. The method of claim 18, wherein activating the subset of elements of the transducer array to emit the neuromodulating energy dose is further based on a presence of a lift-off event of the energy application device with respect to the subject.

23. The method of claim 18, further comprising the acts of:

generating a notification or message to perform one or more of repositioning or reorienting the energy application device in response to a determination that a sufficient portion of the target region is not present in the ultrasound image data or a determination that an ultrasonic therapy beam cannot be sufficiently applied to the target region to administer a therapy dose; and repeating the determination that the target region is present in the ultrasound image data and the determination that the neuromodulating energy dose can be sufficiently applied to the target region until both determinations have a positive result and activating the one or more elements to emit the neuromodulating energy dose.

24. The method of claim 18, further comprising the acts of:

automatically adjusting one or both of a position or orientation of one or more of the elements in response to a determination that a sufficient portion of the target region is not present in the ultrasound image data or a determination that the neuromodulating energy dose cannot be sufficiently applied to the target region; and repeating the determination that the target region is present in the ultrasound image data and the determination that the neuromodulating energy dose can be sufficiently applied to the target region until both determinations have a positive result and subsequently activating some or all of the one or more elements to emit the neuromodulating energy dose.

25. A neuromodulation system, comprising:

an ultrasound energy application device configured to deliver a neuromodulating energy dose to a target region in a subject; and a controller configured to:

receive ultrasound image data of an internal tissue of the subject, wherein the ultrasound image data depicts anatomical structures when reconstructed;

identify the target region in the internal tissue of the subject based on the ultrasound image data;

identify an obstructive anatomical region based on anatomical structures depicted within the ultrasound image data;

upon identifying the target region and the obstructive anatomical region, identify a clear beam path for delivering the neuromodulating energy dose to determine a clearance metric of the clear beam path based on the ultrasound image data, wherein the clear beam path is clear for a first subset of one or more elements of a therapy transducer array of the ultrasound energy application device based on the target region identified in the ultrasound image data and wherein a beam path is obstructed for a second subset of the one or more elements of the therapy transducer array based on the obstructive anatomical region identified based on the ultrasound image data, wherein the obstructive anatomical region is positioned between the second subset and the target region;

compare the clearance metric to one or more safety criteria, therapy dose criteria or an effectiveness threshold to determine if the clear beam path is sufficient for delivering the neuromodulating energy dose along the clear beam path using the first subset of the one or more elements;

dynamically adjusting a duration of treatment based on the clearance metric. wherein the clearance metric corresponds to a percent visibility of the target region in the image data; and activate only the first subset and not the second subset of elements of the transducer array of the ultrasound energy application device to cause the neuromodulation of one or more nerve pathways of the target region for the adjusted duration to achieve a targeted physiological outcome by delivering the neuromodulating energy dose.

* * * * *